(12) United States Patent
Hou et al.

(10) Patent No.: US 12,734,033 B2
(45) Date of Patent: Sep. 15, 2026

(54) AORTIC VALVE REPLACEMENT

(71) Applicant: BOSTON SCIENTIFIC SCIMED, INC., Maple Grove, MN (US)

(72) Inventors: Dongming Hou, Plymouth, MN (US); Tim O'Connor, Galway (IE); Richard O'Sullivan, Turloughmore (IE); Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/508,124

(22) Filed: Oct. 22, 2021

(65) Prior Publication Data

US 2022/0125587 A1 Apr. 28, 2022

Related U.S. Application Data

(60) Provisional application No. 63/104,694, filed on Oct. 23, 2020.

(51) Int. Cl.
*A61F 2/24* (2006.01)

(52) U.S. Cl.
CPC .... *A61F 2/2436* (2013.01); *A61F 2220/0016* (2013.01); *A61F 2230/0091* (2013.01)

(58) Field of Classification Search
CPC ........... A61F 2/2427; A61F 2/243; A61F 2/95
See application file for complete search history.

(56) References Cited

U.S. PATENT DOCUMENTS 6,287,339 B1 * 9/2001 Vazquez ............... A61F 2/2409 623/2.11
8,998,976 B2 4/2015 Gregg et al.
9,204,964 B2 12/2015 Dahlgren et al.
9,750,606 B2 9/2017 Ganesan et al.
10,213,301 B2 2/2019 Ganesan et al.
10,531,952 B2 1/2020 Paul et al.
10,624,642 B2 4/2020 Randhawa
2001/0039450 A1 11/2001 Pavonik et al.
2006/0161249 A1 * 7/2006 Realyvasquez ....... A61F 2/2427 623/1.36
2008/0039934 A1 * 2/2008 Styrc ..................... A61F 2/2418 623/2.38
2010/0249920 A1 * 9/2010 Bolling ................. A61F 2/2445 623/2.11

(Continued)

*Primary Examiner* — Darwin P Erezo
*Assistant Examiner* — Zehra Jaffri
(74) *Attorney, Agent, or Firm* — Seager, Tufte & Wickhem LLP

(57) ABSTRACT

Methods and systems for securing a medical implant at a valve. An illustrative method may include advancing a delivery system though a vasculature to a target location. At the target location, the delivery system may be proximally retracted to expose a medical implant carried within a lumen of the delivery system. The medical implant may be radially expanded from a collapsed delivery configuration an expanded deployed configuration. A fixation mechanism delivery system may be advanced through the vasculature to the target location. A first fixation mechanism configured to engage a native tissue and a portion of the medical implant may be deployed from the fixation mechanism delivery system. After deploying the fixation mechanism, the medical implant may be released from the delivery system.

15 Claims, 19 Drawing Sheets

(56) References Cited

U.S. PATENT DOCUMENTS

2012/0165927 A1* 6/2012 Stocker ................. A61F 2/2418 623/2.11
2014/0046347 A1 2/2014 Cully et al.
2014/0277426 A1* 9/2014 Dakin ..................... A61F 2/246 623/2.38
2015/0018939 A1 1/2015 Colson et al.
2015/0173897 A1* 6/2015 Raanani ................ A61F 2/2436 623/2.11
2017/0042678 A1* 2/2017 Ganesan ............... A61F 2/2439
2018/0028305 A1* 2/2018 von Oepen ............... A61F 2/95
2018/0049873 A1 2/2018 Manash et al.
2018/0071085 A1 3/2018 Rafi et al.
2018/0325663 A1* 11/2018 Taylor ................... A61F 2/2412
2018/0344457 A1* 12/2018 Gross ...................... A61F 2/246
2019/0015205 A1 1/2019 Rajagopal et al.
2019/0110893 A1 4/2019 Haarer et al.
2019/0175209 A1* 6/2019 Guerra .................. A61M 25/09
2020/0188107 A1* 6/2020 Gloss ............... A61B 17/00234

* cited by examiner 200
202
204a
204b
204c
204d
206
208
210
212
214
216
218

AORTIC VALVE REPLACEMENT

CROSS-REFERENCE TO RELATED APPLICATIONS

This application claims the benefit of priority of U.S. Provisional Application No. 63/104,694 filed Oct. 23, 2020, the entire disclosure of which is hereby incorporated by reference.

TECHNICAL FIELD

The present disclosure pertains to medical devices, and methods for manufacturing and/or using medical devices. More particularly, the present disclosure pertains to attachment mechanisms for a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices.

In a first example, a method for securing a medical implant at a valve may comprise advancing a delivery system though a vasculature to a target location, proximally retracting the delivery system to expose a medical implant carried within a lumen of the delivery system, radially expanding the medical implant from a collapsed delivery configuration an expanded deployed configuration, advancing a fixation mechanism delivery system through the vasculature to the target location, deploying a first fixation mechanism from the fixation mechanism delivery system, the first fixation mechanism configured to engage a native tissue and a portion of the medical implant, and after deploying the first fixation mechanism, releasing the medical implant from the delivery system.

Alternatively, or additionally to any of the examples above, in another example, the first fixation mechanism may be a clip assembly.

Alternatively, or additionally to any of the examples above, in another example, the clip assembly may be configured to receive the native tissue and the portion of the medical implant between a pair of clip arms.

Alternatively, or additionally to any of the examples above, in another example, the fixation mechanism delivery system may comprise a commissure clamp catheter.

Alternatively, or additionally to any of the examples above, in another example, the first fixation mechanism may be radially expandable from a delivery configuration to a deployed configuration.

Alternatively, or additionally to any of the examples above, in another example, a first portion of the first fixation mechanism may be configured to be positioned adjacent to an inner surface of the medical implant and a second portion of the first fixation mechanism may be configured to be positioned adjacent to the native tissue.

Alternatively, or additionally to any of the examples above, in another example, the first fixation mechanism may comprise a first expandable basket, a second expandable basket, and an elongate connecting member extending therebetween.

Alternatively, or additionally to any of the examples above, in another example, the first fixation mechanism may comprise a helical winding.

Alternatively, or additionally to any of the examples above, in another example, the first fixation mechanism comprises a first retaining feature, a second retaining feature, and an elastic coil extending between the first and second retaining features.

Alternatively, or additionally to any of the examples above, in another example, the first fixation mechanism may comprise one or more curved tines interconnected through a ring.

Alternatively, or additionally to any of the examples above, in another example, the fixation mechanism delivery system may comprise a delivery needle.

Alternatively, or additionally to any of the examples above, in another example, the fixation mechanism delivery system may further comprise a pigtail catheter.

Alternatively, or additionally to any of the examples above, in another example, the pigtail catheter may comprise an aperture extending through a radially outward surface thereof, the delivery needle may be configured to exit the aperture.

Alternatively, or additionally to any of the examples above, in another example, the method may further comprise deploying a second fixation mechanism and a third fixation mechanism.

Alternatively, or additionally to any of the examples above, in another example, the first fixation mechanism may be configured to engage a first native valve leaflet, the second fixation mechanism may be configured to engage a second native valve leaflet, and the third fixation mechanism may be configured to engage a third native valve leaflet.

In another example, a method for securing a medical implant at a valve may comprise advancing a delivery system though a vasculature to a target location, proximally retracting the delivery system to expose a medical implant carried within a lumen of the delivery system, radially expanding the medical implant from a collapsed delivery configuration an expanded deployed configuration, advancing a commissure clamp catheter through the vasculature to the target location, deploying a first clip assembly from the commissure clamp catheter, the first clip assembly configured to receive a native tissue and a portion of the medical implant between a pair of clip arms, and after deploying the first clip assembly, releasing the medical implant from the delivery system.

Alternatively, or additionally to any of the examples above, in another example, the method may further comprise deploying a second clip assembly and a third clip assembly.

Alternatively, or additionally to any of the examples above, in another example, the first clip assembly may be configured to engage a first native valve leaflet, the second clip assembly may be configured to engage a second native valve leaflet, and the third clip assembly may be configured to engage a third native valve leaflet.

In another example, a method for securing a medical implant at a valve may comprise advancing a delivery system though a vasculature to a target location, proximally retracting the delivery system to radially expand a docking ring carried within a lumen of the delivery system, the docking ring comprising a tubular member including a plurality of apertures and one or more securement barbs extending radially from an outer surface thereof, advancing the delivery system to position a medical implant carried within the lumen of the delivery system adjacent to the docking ring, radially expanding the medical implant from a collapsed delivery configuration an expanded deployed configuration, and releasing the medical implant from the delivery system. An outer surface of the medical implant may be configured to contact and frictionally engage an inner surface of the docking ring.

Alternatively, or additionally to any of the examples above, in another example, the docking ring may further comprise a coating disposed on an inner and/or outer surface thereof.

Alternatively, or additionally to any of the examples above, in another example, the medical implant may comprise a seal disposed over a portion thereof.

Alternatively, or additionally to any of the examples above, in another example, the seal of the medical implant may frictionally engage the coating of the docking ring.

Alternatively, or additionally to any of the examples above, in another example, the one or more securement barbs may be configured to penetrate a native tissue.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
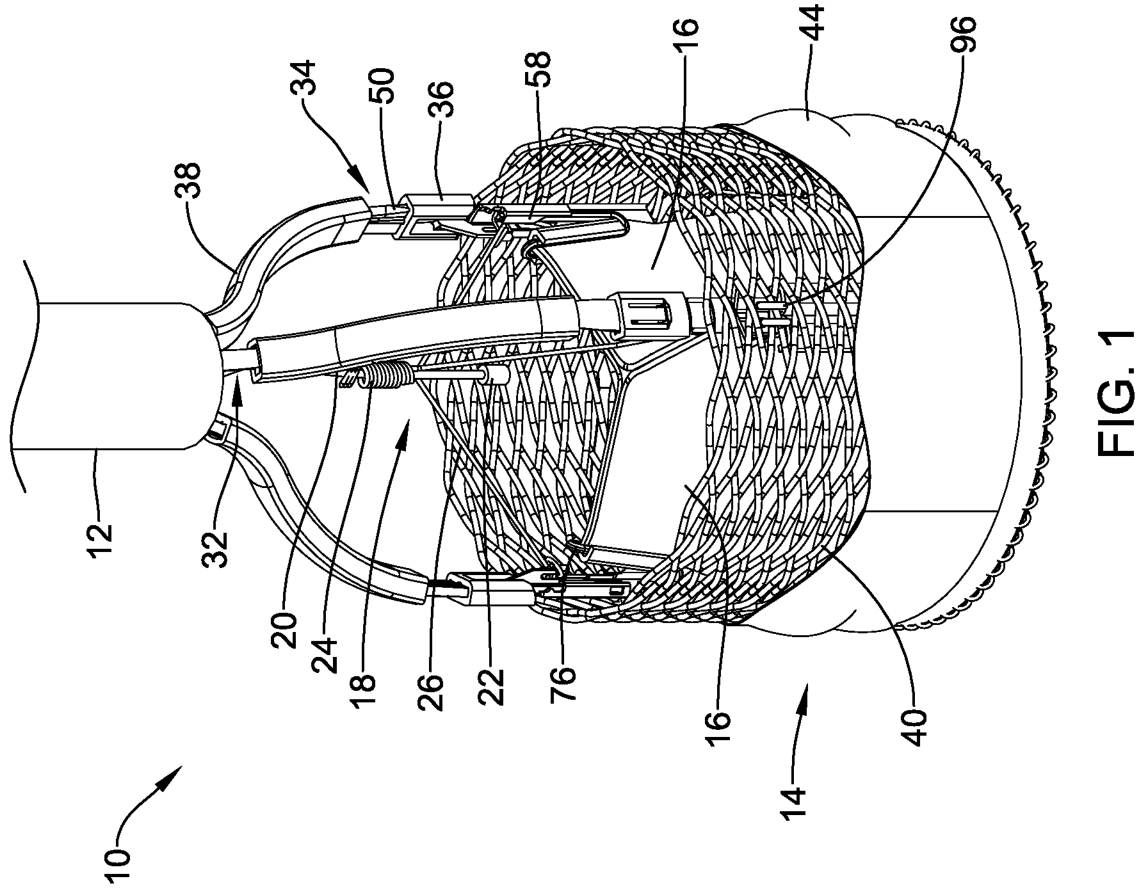
FIG. 1 is a perspective view of a portion of an example implant in a deployed configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Transcatheter aortic valve replacement (TAVR) is used to treat aortic stenosis in a growing number of patients. Generally, pure aortic regurgitation (PAR) is considered a relative contraindication for TAVR. Aortic regurgitation (AR) may be a relatively prevalent source of cardiovascular morbidity and mortality and may be found in up to 13.0% and 8.5% of American men and women, respectively. AR may be associated with increased complications for patients undergoing TAVR due to increased risk for embolization, valve migration, and post-procedural regurgitation. This risk may be accentuated by the lack of calcification present in patients with AR, as opposed to aortic stenosis TAVR patients, making device placement difficult as TAVR valves are anchored into place by native valve calcification. The present disclosure is directed to an artificial valve for use in the management of native AR by utilizing a calcification-independent anchoring mechanism. While the present disclosure is described with respect to aortic valve replacement, it is contemplated that the devices and methods described herein may be used in other anatomical locations, as desired.

FIG. 1 is a perspective view of a portion of an example medical implant system 10. It should be noted that some features of the medical implant system 10 are either not shown, or are shown schematically, in FIG. 1 for simplicity. A medical implant system 10 may be used to deliver and/or deploy a variety of medical devices to a number of locations within the anatomy. In at least some embodiments, the medical implant system 10 may be a replacement heart valve system (e.g., a replacement aortic valve system) that can be used for percutaneous delivery of a replacement heart valve. This, however, is not intended to be limiting as the medical implant system 10 may also be used for other interventions including mitral valve replacement, valve repair, valvuloplasty, and the like, or other similar interventions.

The medical implant system 10 may generally be described as a catheter system that includes a delivery system 12 and a medical implant 14 (such as, but not limited to, a valve replacement implant) which may be coupled to the delivery system 12 and disposed within a lumen of the delivery system 12 during delivery of the medical implant 14. In some embodiments, a handle or actuator may be disposed at a proximal end of the delivery system 12. In general, the handle may be configured to manipulate the position of the delivery system 12, as well as aid in the deployment of the medical implant 14.

Prior to use of the medical implant system 10, the patient may be screened using a computerized tomography (CT) scan and/or an echocardiogram. In use, the medical implant system 10 may be advanced percutaneously through the vasculature to a position adjacent to an area of interest via an arterial access, such as, but not limited to, the femoral or radial artery. For example, the medical implant system 10 may be advanced through the vasculature and across the aortic arch to a position adjacent to a defective aortic valve (or other heart valve). During delivery, the medical implant 14 may be generally disposed in an elongated and low profile "delivery" configuration within the delivery system 12. Once positioned, the delivery system 12 may be retracted to expose the medical implant 14. The medical implant 14 may be actuated in order to radially expand the medical implant 14 into a generally shortened and larger cross-sectional profile "deployed" configuration suitable for implantation within the anatomy (as shown in FIG. 1, for example). When the medical implant 14 is suitably deployed within the anatomy, the delivery system 12 can be removed from the vasculature, leaving the medical implant 14 in place in a "released" configuration to function as, for example, a suitable replacement for the native aortic valve. In at least some interventions, the medical implant 14 may be deployed within the native valve (e.g., the native valve is left in place and not excised). Alternatively, the native valve may be removed and the medical implant 14 may be deployed in its place as a replacement.

In some embodiments, the delivery system 12 may include one or more lumens extending therethrough. For example, in some embodiments, the delivery system 12 may include a first lumen, a second lumen, a third lumen, and a fourth lumen. In general, the one or more lumens extend along an entire length of the delivery system 12. Other embodiments are contemplated, however, where one or more of the one or more lumens extend along only a portion of the length of the delivery system 12. For example, in some embodiments, the fourth lumen may stop just short of a distal end of the delivery system 12 and/or be filled in at its distal end to effectively end the fourth lumen proximal of the distal end of the delivery system 12.

Disposed within a first lumen of the delivery system 12 may be at least one actuator member, such as an actuator member 50 for example, which may be used to actuate (i.e., expand and/or elongate) the medical implant 14 between a delivery configuration and a deployed configuration. In some cases, the actuator member(s) 50 may herein be referred to, or used interchangeably with, the term "actuator element". In other words, the medical implant system 10 may include at least one actuator member 50. In some embodiments, the at least one actuator member 50 may include two actuator members 50, three actuator members 50, four actuator members 50, or another suitable or desired number of actuator members 50. For the purpose of illustration only, the medical implant system 10 and/or the medical implant 14 is shown with three actuator members 50.

In at least some embodiments, the first lumen may be lined with a low friction liner (e.g., a fluorinated ethylene propylene (FEP) liner). Disposed within a second lumen may be a pin release mandrel 20. In at least some embodiments, the second lumen may be lined with a hypotube liner. A third lumen may be a guidewire lumen and, in some embodiments, the third lumen may also be lined with a hypotube liner. In some embodiments, a fourth lumen may be used to house a non-stretch wire or other reinforcing member. The form of the non-stretch wire or other reinforcing member may vary. In some embodiments, the non-stretch wire may take the form of a stainless steel braid. The non-stretch wire may optionally include a pair of longitudinally-extending aramid and/or para-aramid strands (for example, KEVLAR®) disposed on opposite sides of the braid. In general, rather than being "disposed within" the fourth lumen, the non-stretch wire may be embedded within the fourth lumen. In addition, the non-stretch wire may extend to a position adjacent to a distal end region but not fully to the distal end of the delivery system 12. For example, a short distal segment of the fourth lumen may be filled in with polymer material adjacent to the distal end of the delivery system 12.

The delivery system 12 may also include a guidewire tube extension that extends distally from the distal end region. In some embodiments, a nose cone may be attached to the guidewire tube extension. In some embodiments, the nose cone generally is designed to have an atraumatic shape. In some embodiments, the nose cone may also include a ridge or ledge that is configured to abut the distal tip of the delivery system 12 during delivery of the medical implant 14.

FIG. 1 illustrates some selected components of the medical implant system 10 and/or the medical implant 14. For example, here it can be seen that the medical implant 14 may include a plurality of valve leaflets 16 (e.g., bovine pericardial) which may be secured to a tubular anchor member or braid 40 that is reversibly actuatable between a "delivery" configuration and a "deployed" configuration. In some embodiments, the anchor member or braid 40 may be substantially cylindrical in shape or configuration. Some suitable but non-limiting materials for the anchor member or braid 40, for example metallic materials or polymeric materials, may be described below. In some embodiments, the medical implant 14 may include a plurality of locking mechanisms configured to secure the anchor member or braid 40 in the "deployed" configuration. In some embodiments, the at least one actuator member 50 may be configured to engage with the plurality of locking mechanisms and actuate the anchor member or braid 40 between the "delivery" configuration and the "deployed" configuration. In some embodiments, one actuator member 50 may correspond to, engage with, and/or actuate one locking mechanism. In some embodiments, one actuator member 50 may correspond to, engage with, and/or actuate more than one locking mechanism. Other configurations are also contemplated.

While a plurality of actuator members 50 and/or corresponding locking mechanisms may be included in a medical implant 14, for clarity and brevity, much of the following discussion will be limited to a single instance of these elements. The skilled person will readily recognize that the features and operation of the examples discussed below may apply equally to and across all instances of the plurality of locking mechanisms and/or the plurality of actuator members 50. Some suitable but non-limiting materials for the plurality of locking mechanisms and/or the plurality of actuator members 50, for example metallic materials or polymeric materials, may be described below.

In some embodiments, the plurality of locking mechanisms may each comprise an axially movable post member 76, for example at the commissure portions of the valve leaflets 16 (post member 76 may sometimes be referred to as a "commissure post"), and a buckle member 58 fixedly attached to the anchor member or braid 40. In other words, in at least some embodiments, a medical implant 14 may include a plurality of post members 76 and a corresponding plurality of buckle members 58. Other configurations and correspondences are also contemplated. In some embodiments, the post member 76 may engage the buckle member 58 in the "deployed" configuration. In some embodiments, the post member 76 may be axially or longitudinally spaced apart from the buckle member 58 in the "delivery" configuration. Some suitable but non-limiting materials for the post member 76 and/or the buckle member 58, for example metallic materials or polymeric materials, may be described below.

In some embodiments, a distal end of the axially movable post member 76 may be secured and/or attached (i.e., fixedly attached, movably attached, removably attached, etc.) to a distal portion of the anchor member or braid 40, such as by a suture, a tether, adhesives, or other suitable element 96. In some embodiments, the post member 76 may be axially or longitudinally movable relative to the anchor member or braid 40 and/or the buckle member 58 may be fixedly attached to the anchor member or braid 40. Other embodiments are contemplated where the buckle member 58 may be movably or removably attached to the anchor member or braid 40. In some embodiments, the post member 76 may be fixedly attached to the anchor member or braid 40 and the buckle member 58 may be fixedly attached to the anchor member or braid 40. In some embodiments, one of the post member 76 and the buckle member 58 may be fixedly attached to the anchor member or braid 40 and the other may be movably or removably attached to the anchor member or braid 40. In some embodiments, the post member 76 may be movably or removably attached to the anchor member or braid 40 and the buckle member 58 may be movably or removably attached to the anchor member or braid 40. In some embodiments, the post member 76 may be secured or attached (i.e., fixedly attached, movably attached, removably attached, etc.) to a distal end of the anchor member or braid 40. In some embodiments, the buckle member 58 may be fixed or attached to a proximal portion of the anchor member or braid 40. In some embodiments, the buckle member 58 may be fixed or attached at or to a proximal end of the anchor member or braid 40.

In some embodiments, the medical implant 14 may include one or more of the plurality of valve leaflets 16 secured to the anchor member or braid 40 at, adjacent to, and/or using (at least in part) individual, corresponding post members 76. The valve leaflets 16 may also be secured to a base, or the distal end, of the anchor member or braid 40. Positioned adjacent to (e.g., aligned with) the plurality of post members 76 is a corresponding plurality of buckle members 58. In the illustrated examples, one buckle member 58 is attached to the anchor member or braid 40 adjacent to each of the three post members 76. Accordingly, the anchor member or braid 40 has a total of three buckle members 58 and three post members 76 attached thereto. Similarly, one actuator member 50 may be operatively associated with each post member 76 and buckle member 58, for a total of three actuator members 50 in the illustrated example. Other embodiments are contemplated where fewer or more buckle members 58, post members 76, and actuator members 50 may be utilized. In some embodiments, a seal 44 may be disposed about the anchor member or braid 40 and, as the term suggests, may help to seal the medical implant 14 within and/or against a target site or area of interest upon deployment.

In some embodiments, attachment between the medical implant 14 and the delivery system 12 may be effected through the use of a coupler 32. In some embodiments, the coupler 32 may generally include a cylindrical base (not shown) that may be disposed about and/or attached to the delivery system 12. Projecting distally from the base is a plurality of fingers 34 (e.g., two, three, four, etc.) that are each configured to engage with the medical implant 14 at a proximal end of one of the buckle members 58. A collar 36 may be disposed about the fingers 34 of the coupler 32 to further assist in holding together the fingers 34 and the buckle members 58. A guide 38 may be disposed over each of the fingers 34 proximal of the collar 36 and may serve to keep the fingers 34 of the coupler 32 associated with the plurality of actuator members 50 extending adjacent to (and axially slidable relative to) the fingers 34 of the coupler 32. Finally, a pin release assembly 18 may be a linking structure that keeps post members 76, buckle members 58, and actuator members 50 associated with one another. In some embodiments, the pin release assembly 18 may include a plurality of individual pin members 26 that may be joined together via a coiled connection 24 and held to a pin release mandrel 20 with a ferrule 22. Some suitable but non-limiting materials for the coupler 32, the plurality of fingers 34, the collar 36, the guide 38, the pin release assembly 18, the plurality of individual pin members 26, the pin release mandrel 20 and/or the ferrule 22, for example metallic materials or polymeric materials, may be described below.

During delivery, the medical implant 14 may be secured at the distal end of the delivery system 12 by virtue of the association of the fingers 34 of the coupler 32 being coupled with a projecting proximal end of the buckle member 58 (and being held in place with the collar 36 disposed over the connection) and by virtue of the pin members 26 securing together the plurality of actuator members 50 and the post members 76. When the medical implant 14 is advanced to the target site or area of interest, the delivery system 12 may be withdrawn or retracted to expose the medical implant 14 (or the medical implant 14 may be advanced distally relative to the delivery system 12). Then, the plurality of actuator members 50 can be used to axially shorten and/or radially expand and "lock" the medical implant 14 and/or the anchor member or braid 40 from the "delivery" configuration to an expanded or "deployed" configuration (as shown in FIG. 1, for example) by proximally retracting the plurality of actuator members 50 to pull the post members 76 into engagement with the buckle members 58. Finally, the pin members 26 can be removed, thereby uncoupling the plurality of actuator members 50 from the post members 76, which allows the plurality of actuator members 50 and the fingers 34 of the coupler 32 to be withdrawn from the medical implant 14 thereby deploying the medical implant 14 (and/or the anchor member or braid 40) at the target site or area of interest in a "released" configuration. In other words, one difference between the "deployed" configuration and the "released" configuration is whether or not the pin members 26 are attached to the post members 76. In the "deployed" configuration, the pin members 26 are still attached to the post members 76, which thus permits the medical implant 14 (and/or the anchor member or braid 40) to be unlocked via distal advancement of the plurality of actuator members 50, in order to reposition the medical implant 14, for example. In some embodiments, at least a portion of the plurality of valve leaflets 16 may axially or longitudinally overlap at least a portion of the buckle members 58 at a common position along a central longitudinal axis of the anchor member or braid 40, which in some embodiments may allow for a shorter overall length or height of the medical implant 14.

Figure 2:
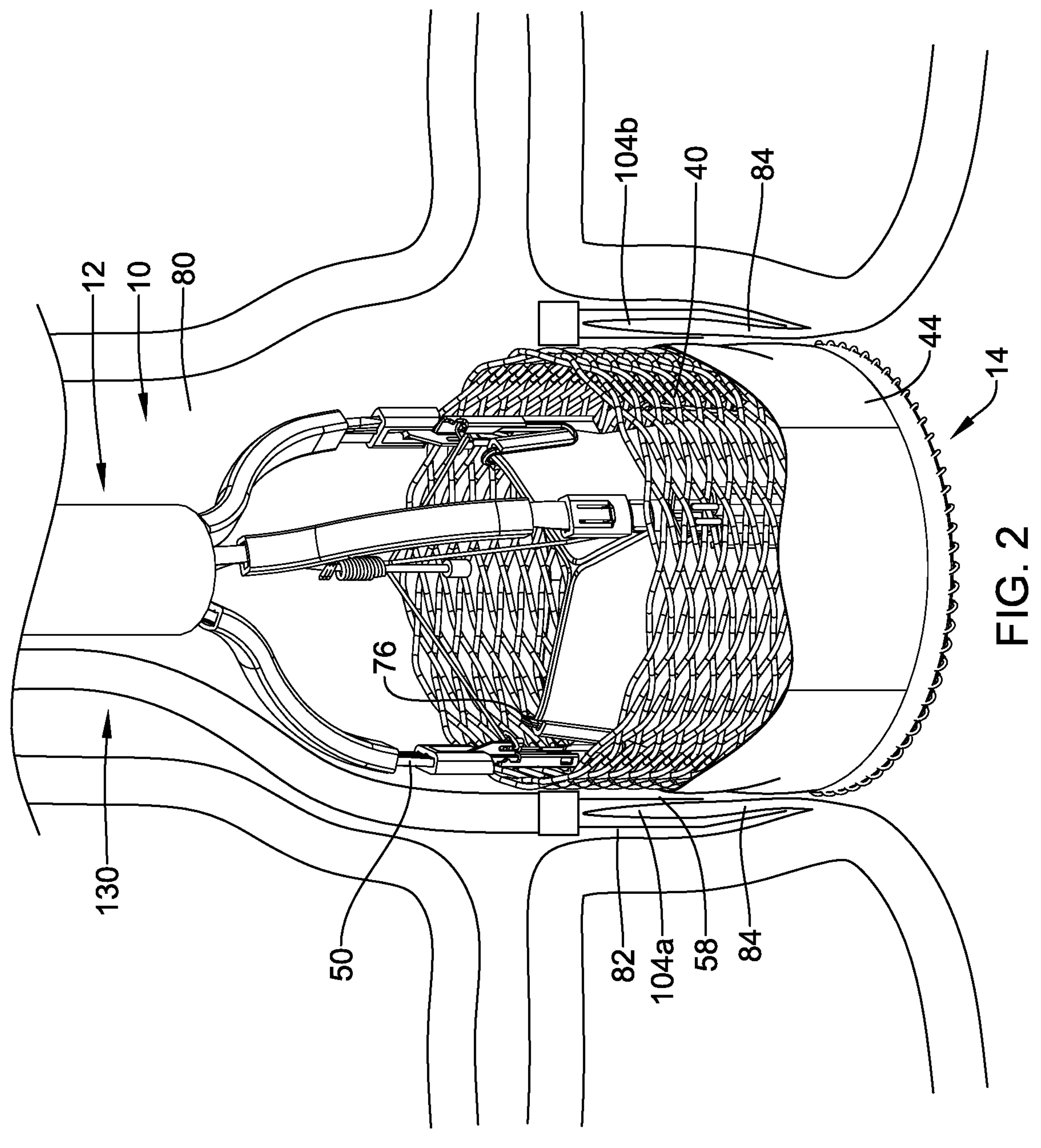
FIG. 2 is a schematic view of the illustrative implant of FIG. 1 in a deployed configuration within the body.

FIG. 2 illustrates a schematic view of the illustrative medical implant system 10 including at least a delivery system 12 and a medical implant 14 in a deployed configuration at the aortic valve 82. As described above, prior to use of the medical implant system 10, the patient may be screened using a CT scan and/or an echocardiogram. An arterial access may be used to deliver the system through the vasculature. Generally, the delivery system 12 may be advanced through the vasculature and steered into or towards the aortic arch 80 via the femoral artery with the medical implant 14 in a collapsed delivery configuration within the delivery system 12. In some cases, the delivery system 12 may be advanced over a guidewire, although this is not required. In some implementations, the guidewire and the delivery system 12, a pigtail catheter (not explicitly shown), and/or other devices may be tracked together, with the guidewire leading the delivery system 12 (e.g., advance the guidewire a distance, then advance the delivery system 12 over the guidewire approximately the same distance). In some cases, where the guidewire is floppy or lacks rigidity, it may be introduced inside the delivery system 12 and then advanced ahead of other devices in the vasculature.

The delivery system 12 may be advanced into the descending portion of the aortic arch 80. When so provided, a pigtail catheter may then be advanced through the delivery system 12 (if it was not advanced with or prior to the delivery system 12). In some embodiments, the pigtail catheter may be advanced into the ascending portion of the aortic arch 80 where it may deliver a radiopaque fluid or contrast fluid to facilitate visualization of the procedure. In other embodiments, the pigtail catheter may be positioned at or against the cusps or leaflets 84 of the aortic valve 82. For example, one or more pigtail catheters may be positioned at the non-coronary cusp (NCC) and/or the right coronary cusp (RCC). Tracking of the delivery system 12 may be performed under fluoroscopy, for example using radiopaque markers (e.g., at a distal end of the delivery system 12) and/or radiopaque fluid or contrast media. Radiopaque fluid or contrast media may be provided through the pigtail catheter and/or the delivery system 12. In some cases, the radiopaque fluid or contrast media may be used to perform an aortogram prior to inserting a guidewire or TAVR wire and then advancing the medical implant 14.

Once the medical implant 14 is at or adjacent to the target location, the delivery system 12 may be withdrawn or retracted to expose the medical implant 14 (or the medical implant 14 may be advanced distally relative to the delivery system 12). Then, the plurality of actuator members 50 can be used to axially shorten and/or radially expand and lock the medical implant 14 and/or the anchor member or braid 40 from the delivery configuration to an expanded or deployed configuration (as shown in FIG. 2, for example) by proximally retracting the plurality of actuator members 50 to pull the post members 76 into engagement with the buckle members 58, as described above. It is contemplated that the medical implant 14 may displace the leaflets 84 of the native valve 82 or the leaflets 84 may be excised. Once the medical implant 14 is fully locked, the medical implant 14 may be a fully functional valve capable of maintaining hemodynamic stability while still being coupled to the delivery system 12.

It is contemplated that prior to moving the medical implant 14 from the deployed configuration to the released configuration, it may be desirable to secure the medical implant 14 to the adjacent tissue. In some cases, one or more fixation mechanisms or clip assemblies 104*a*, 104*b* (collectively, 104) may be used to secure the medical implant 14 to the adjacent tissue. In some instances, the fixation mechanism may be a hemostasis clip, such as, but not limited to the Resolution™ Clip or the Resolution 360™ made by Boston Scientific, Corporation. While the fixation mechanism 104 is described as a clip, it is contemplated that any structure that allows for attachment of the medical implant 14 to the native tissue may be used.

To deploy a clip assembly 104, a commissure clamp catheter, or fixation mechanism delivery system 130 may be advanced through the vasculature to the implant location of the medical implant 14. In some cases, the commissure clamp catheter 130 may be advanced through the vasculature external to the delivery system 12, as shown in FIG. 2. In other cases, the commissure clamp catheter 130 may be advanced through a lumen of the delivery system 12. The commissure clamp catheter 130 may be used to deliver one or more clip assemblies 104 to secure the medical implant 14 to the native tissue. The clip assemblies 104 may be configured to grip both native tissue (such, as but not limited to, a native leaflet 84) and a portion of the medical implant 14.

Generally, a clip assembly 104 may be loaded into or coupled to a distal end of the commissure clamp catheter 130. The commissure clamp catheter 130 may then be advanced (e.g., through the vasculature or through a lumen of the delivery system 12) such that the clip assembly 104 is adjacent to the target location. The clip assembly 104 may then be deployed. In some cases, deploying the clip may include rotating a portion of the commissure clamp catheter 130 to release the clip assembly 104. In other cases, an axially displaced mechanism may be utilized to release the clip assembly 104. These are just some examples. Other release mechanisms may be used, as desired.

In some cases, the clip assemblies 104 may be positioned at or near one or more of the commissures (e.g., where the valve leaflets 16 of the medical implant 14 abut) of the medical implant 14. A same commissure clamp catheter 130 may be used to deliver a plurality of clip assemblies 104. For example, a first clip assembly 104*a* may be deployed or secured to the medical implant 14 and the native tissue, the commissure clamp catheter 130 removed from body, and a second clip assembly 104*b* loaded into the commissure clamp catheter 130. The commissure clamp catheter 130 may then be advanced through the vasculature or the delivery system 12 to the target location to deploy the second clip assembly 104*b*. This may be repeated for the desired number of clip assemblies 104. An illustrative clip delivery system is described in commonly assigned U.S. Pat. No. 10,624,642, titled HEMOSTASIS RELOADABLE CLIP RELEASE MECHANISM, the disclosure of which is hereby incorporated by reference.

Figure 3:
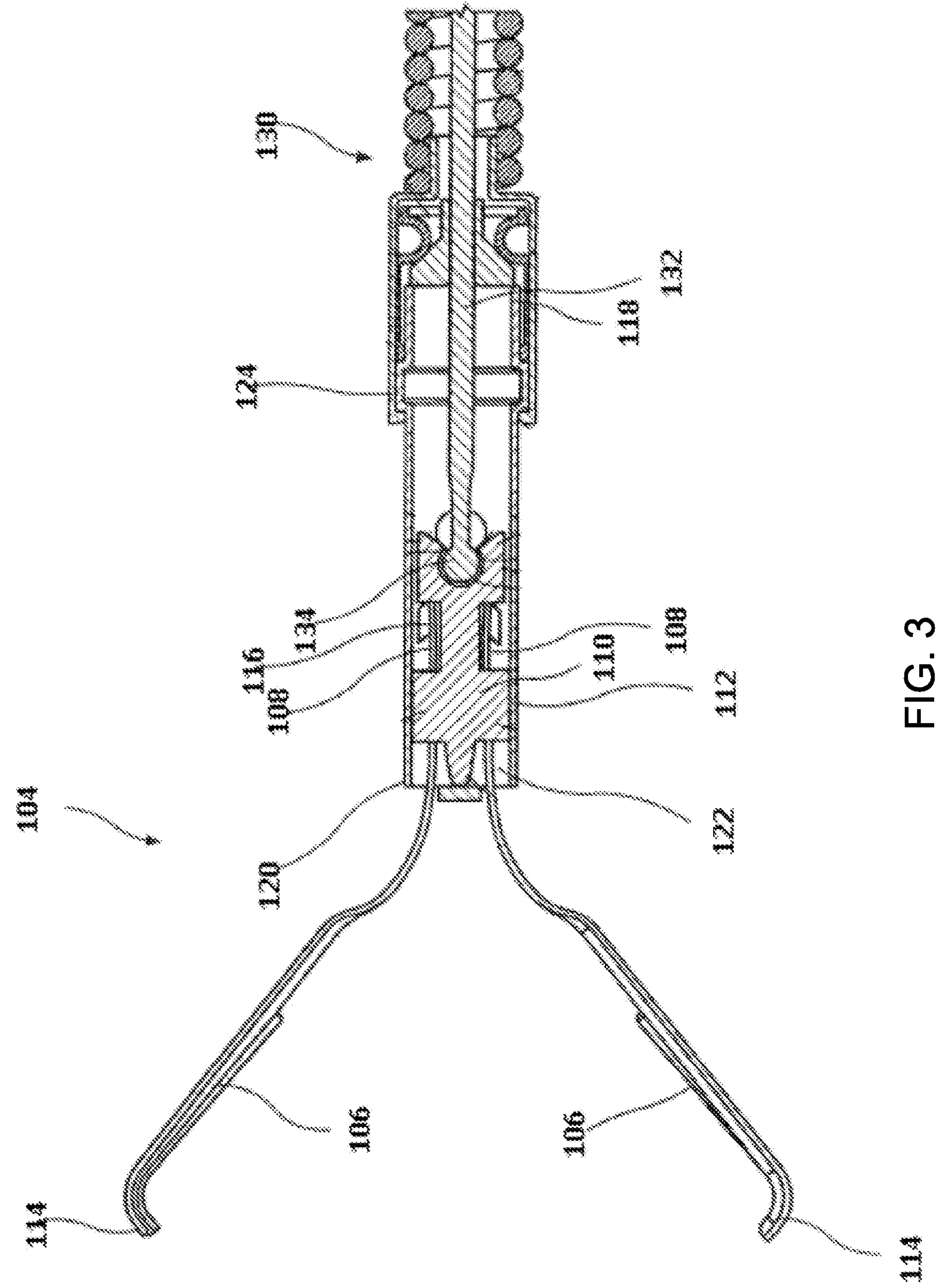
FIG. 3 is a partial cross-section view of an illustrative commissure clamp catheter.

FIG. 3 illustrates a cross-sectional view of an illustrative clip assembly 104 and a distal end region of an illustrative commissure clamp catheter 130. The clip assembly 104 may be loadable onto a distal portion of the commissure clamp catheter 130. The commissure clamp catheter 130 may be configured such that, after deployment of the clip assembly 104 at the target region (e.g., the aortic valve or other treatment area), a new clip assembly 104 may be loaded onto the commissure clamp catheter 130 so that the same commissure clamp catheter 130 may be used to deliver a new clip assembly 104 to a second portion of target region. The clip assembly 104 may include a pair of clip arms 106, proximal ends 108 of which are, in this embodiment, connected to a yoke 110 slidably received within a capsule 112. The clip arms 106 may be biased so that distal ends 114 thereof move apart from one another into a tissue receiving configuration when not drawn into the capsule 112. When drawn into the capsule 112, an interior surface of the capsule 112 may constrain the clip arms 106, holding the distal ends 114 thereof together in a tissue clipping configuration. The yoke 110 may be longitudinally slidable within the capsule 112 to move the clip arms 106 between the tissue receiving configuration and the tissue clipping configuration.

Each of the clip arms 106 may extend from a proximal end 108 to a distal end 114. The distal ends 114 of each of the clip arms 106 may project laterally inward toward the distal end 114 of the other of the clip arms 106 to facilitate gripping of target tissue therebetween. However, this is not required. The distal ends 114 may further include other gripping features such as, for example, teeth and/or protrusions. The clip arms 106 may include features for locking the clip arms 106 within the capsule 112 in the tissue gripping configuration. For example, each of the proximal ends 108 of the clip arms 106 may include a locking tab 116 extending laterally outward therefrom. The clip arms 106 are biased so that, when the clip arms 106 are being locked in the tissue clipping configuration, the locking tab 116 of each of the clip arms 106 springs outward to lockingly engage a portion of the capsule 112. Engagement of the locking tabs 116 with the capsule 112 locks the clip assembly 104 in the tissue clipping configuration to securely grip any tissue and/or medical device (such as, but not limited to, medical implant 14) received between the distal ends 114 of the clip arms 106 and prevents the clip arms 106 from being moved proximally out of the capsule 112. Moving the yoke 110 relative to the capsule 112 correspondingly moves the clip arms 106 relative to the capsule 112 so that the clip arms 106 may be moved between the tissue receiving and the tissue clipping configurations via movement of the yoke 110.

The yoke 110 may be configured to receive an enlarged end 134 of a control member 132 of the commissure clamp catheter 130. In one exemplary embodiment, the enlarged end 134 may be configured as a ball which is received within a correspondingly sized and shaped socket of the yoke 110. Longitudinal movement of the control member 132 relative to the capsule 112 may control movement of the clip arms 106 between the tissue receiving and the tissue clipping configurations.

The capsule 112 extends longitudinally from a proximal end 118 to a distal end 120 and includes a channel 122 extending longitudinally therethrough. The channel 122 may be sized and shaped to receive the yoke 110 and at least a proximal portion of the clip arms 106 therein. The proximal ends 108 of the clip arms 106 may be permitted to spring outward, at least in part, until the locking tabs 116 engage an interior of the increased diameter portion 124, thereby locking the clip assembly 104 in the tissue clipping configuration. The increased diameter portion 124 is positioned along the capsule 112 so that the clip arms 106 may be repeatedly moved between the tissue receiving and the clipping configurations until it is desired to lock the clip assembly 104 in the tissue clipping configuration by moving the control wire enlarged end 134 further proximally so that the locking tabs 116 engage the increased diameter portion 124. To release the clip assembly 104 from the commissure clamp catheter 130, the control member 132 may be proximally retracted until the enlarged distal end 134 disengages the yoke 110. Further proximal actuation of the control member 132 may then disengage the capsule 112 from the yoke 110 (and thus the clip assembly 104).

Returning to FIG. 2, in some cases, at least one clip assembly 104 may be positioned at each commissure of the medical implant 14. In such an instance, a medical device 14 having three commissures may have three clip assemblies 104. In other cases, one or more of the commissures may have more than one clip assembly 104 secured adjacent thereto. It is further contemplated that some commissures may be free from a clip assembly 104. For example, one, two, three, four, five, six, or more clip assemblies 104 may be used to secure the medical implant 14 to the body tissue. It is contemplated that the clip assemblies 104 may be coupled to the commissure posts 76, the braid 40, one or more sutures 96 (see, for example, FIG. 1) that have been used to secure the commissure posts 76 to the braid 40, etc. Other portions of the medical implant 14 may be used as desired.

Figure 4:
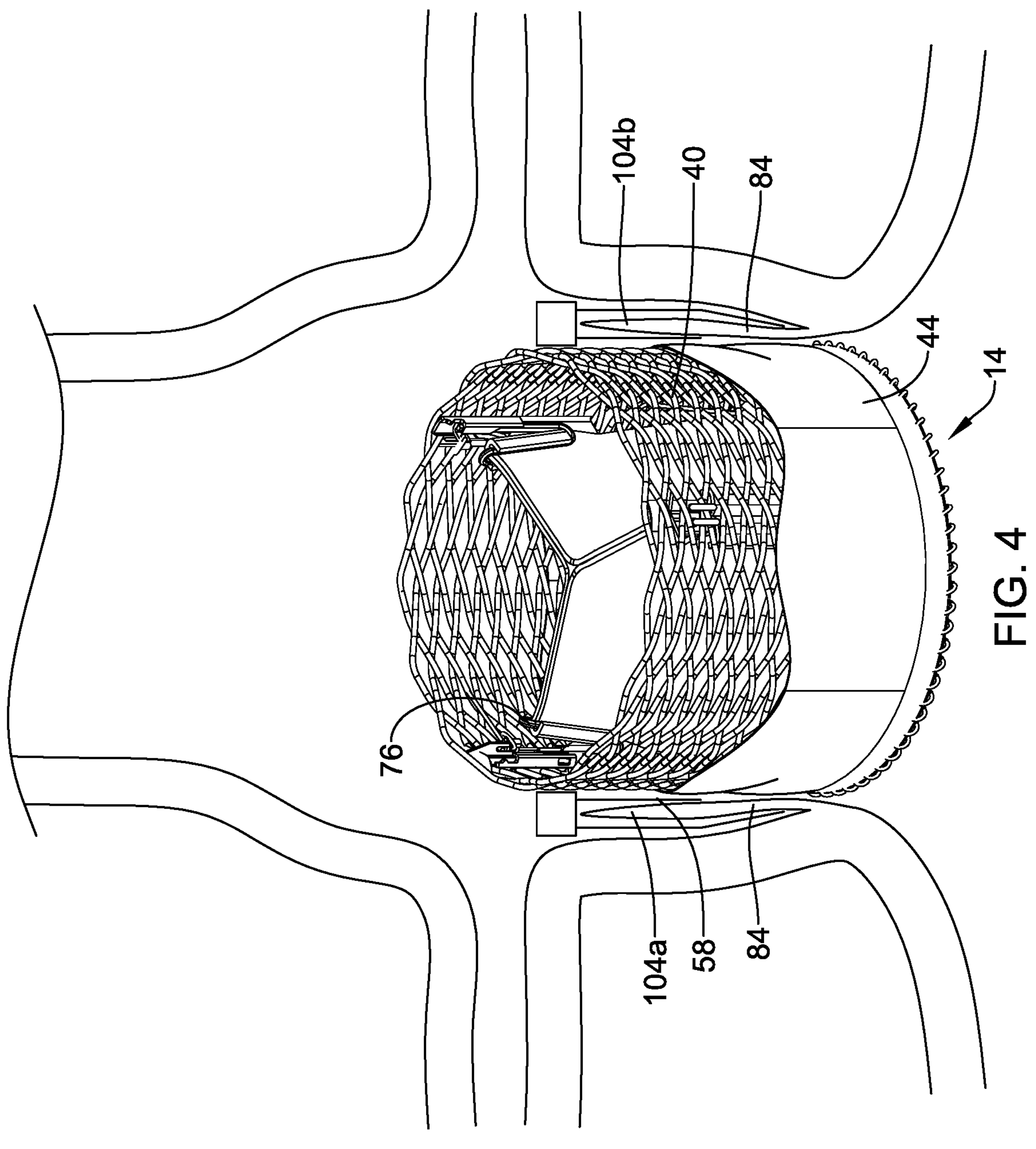
FIG. 4 is a schematic view of the illustrative implant of FIG. 1 in a deployed configuration within the body with a clip assembly.

Once the clip assemblies 104 have been deployed (e.g., secured to the medical implant 14 and the native tissue), the clinician may test the stability of the medical implant 14. If the medical implant 14 is not stable or considered to be at risk of dislodgment, the clinician may secure additional clip assemblies 104 to the medical implant 14 and native tissue. Once the medical implant 14 is stable, the clinician may then move the medical implant 14 from the "deployed" configuration to the "released" configuration, as shown in FIG. 4. After the medical implant 14 is released, the delivery system 12 and any other components (including but not limited to the commissure clamp catheter 130, pigtail catheters, guidewires, etc.) may be removed, if they have not already been removed.

FIGS. 5-12 illustrate an alternative method and system for anchoring a medical implant 14 at or near the aortic valve 82. While FIGS. 5-12 are described with respect to the aortic valve 82, it is contemplated that the method and system may be used in other anatomical locations, as desired. The delivery system 12 and the medical implant 14 may be delivered in a similar manner as described above. Generally, the delivery system 12 may be steered into or towards the aortic arch 80 via the femoral artery with the medical implant 14 in a collapsed delivery configuration within the delivery system 12. In some cases, the delivery system 12 may be advanced over a guidewire, although this is not required. In some implementations, the guidewire and the delivery system 12, a pigtail catheter 200, and/or other devices may be tracked together, with the guidewire leading the delivery system 12 (e.g., advance the guidewire a distance, then advance the delivery system 12 over the guidewire approximately the same distance). In some cases, where the guidewire is floppy or lacks rigidity, it may be introduced inside the delivery system 12 and then advanced ahead of other devices in the vasculature.

The delivery system 12 may be advanced into the descending portion of the aortic arch 80. When so provided, a pigtail catheter 200 may then be advanced through the delivery system 12 (if it was not advanced with the delivery system 12). In some cases, the pigtail catheter 200 may be advanced through the vasculature exterior to, or alongside, the delivery system 12. In some embodiments, the pigtail catheter 200 may be advanced into the ascending portion of the aortic arch 80 where it may deliver a radiopaque fluid or contrast fluid to facilitate visualization of the procedure. A distal end region 202 of pigtail catheter 200 may have a generally arcuate shape (although this is not required) and include one or more apertures 204*a*, 204*b*, 204*c*, 204*d* (collectively, 204) therein. The one or more apertures 204 may be in fluid communication with a lumen of the pigtail catheter 200 and may be configured to deliver the radiopaque fluid or contrast fluid. In other embodiments, the pigtail catheter 200 may be positioned at or against the cusps or leaflets 84 of the aortic valve 82. In some embodiments, the pigtail catheter 200 may be delivered to a first location for delivery of a radiopaque fluid or contrast fluid and a second location for delivery of an anchoring device, as will be described in more detail herein. Tracking of the delivery system 12 may be performed under fluoroscopy, for example using radiopaque markers (e.g., at a distal end of the delivery system 12) and/or radiopaque fluid or contrast media. Radiopaque fluid or contrast media may be provided through the pigtail catheter 200 and/or the delivery system 12.

Figure 5:
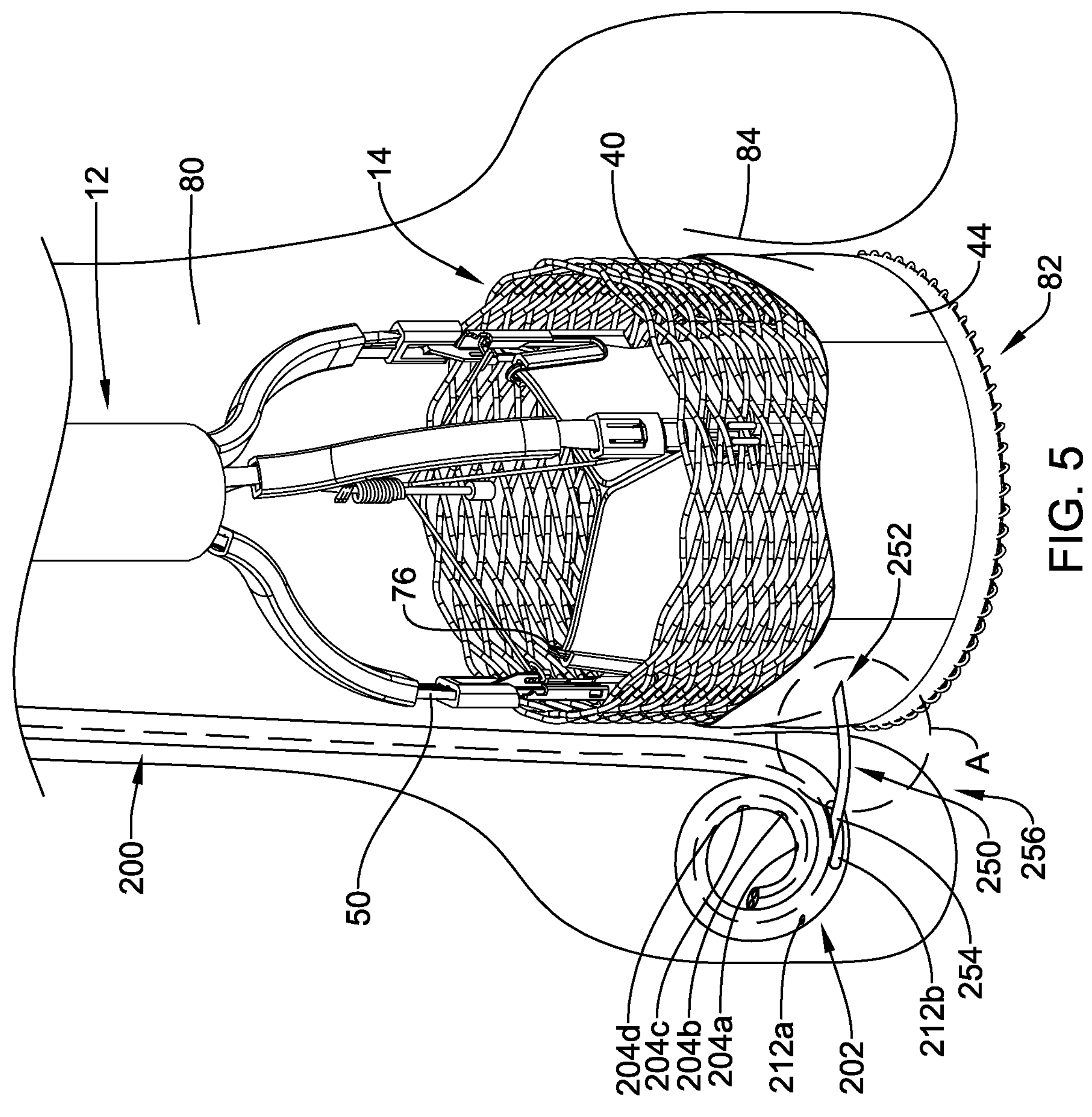
FIG. 5 is a schematic view of the illustrative implant of FIG. 1 in a deployed configuration within the body with an illustrative fixation member delivery system.

Once the medical implant 14 is at or adjacent to the target location, the delivery system 12 may be withdrawn or retracted to expose the medical implant 14 (or the medical implant 14 may be advanced distally relative to the delivery system 12). While FIG. 5 illustrates the pigtail catheter 200 adjacent to the aortic valve 82, during deployment of the medical implant, the pigtail catheter 200 may be positioned in the aortic arch 80 or another position, as desired. The plurality of actuator members 50 can be used to axially shorten and/or radially expand and lock the medical implant 14 and/or the anchor member or braid 40 from the delivery configuration to an expanded or deployed configuration (as shown in FIG. 5, for example) by proximally retracting the plurality of actuator members 50 to pull the post members 76 into engagement with the buckle members 58, as described above. It is contemplated that the medical implant 14 may displace the leaflets 84 of the native valve 82 or the leaflets 84 may be excised. Once the medical implant 14 is fully locked, the medical implant 14 may be a fully functional valve capable of maintaining hemodynamic stability while still being coupled to the delivery system 12.

Figure 6:
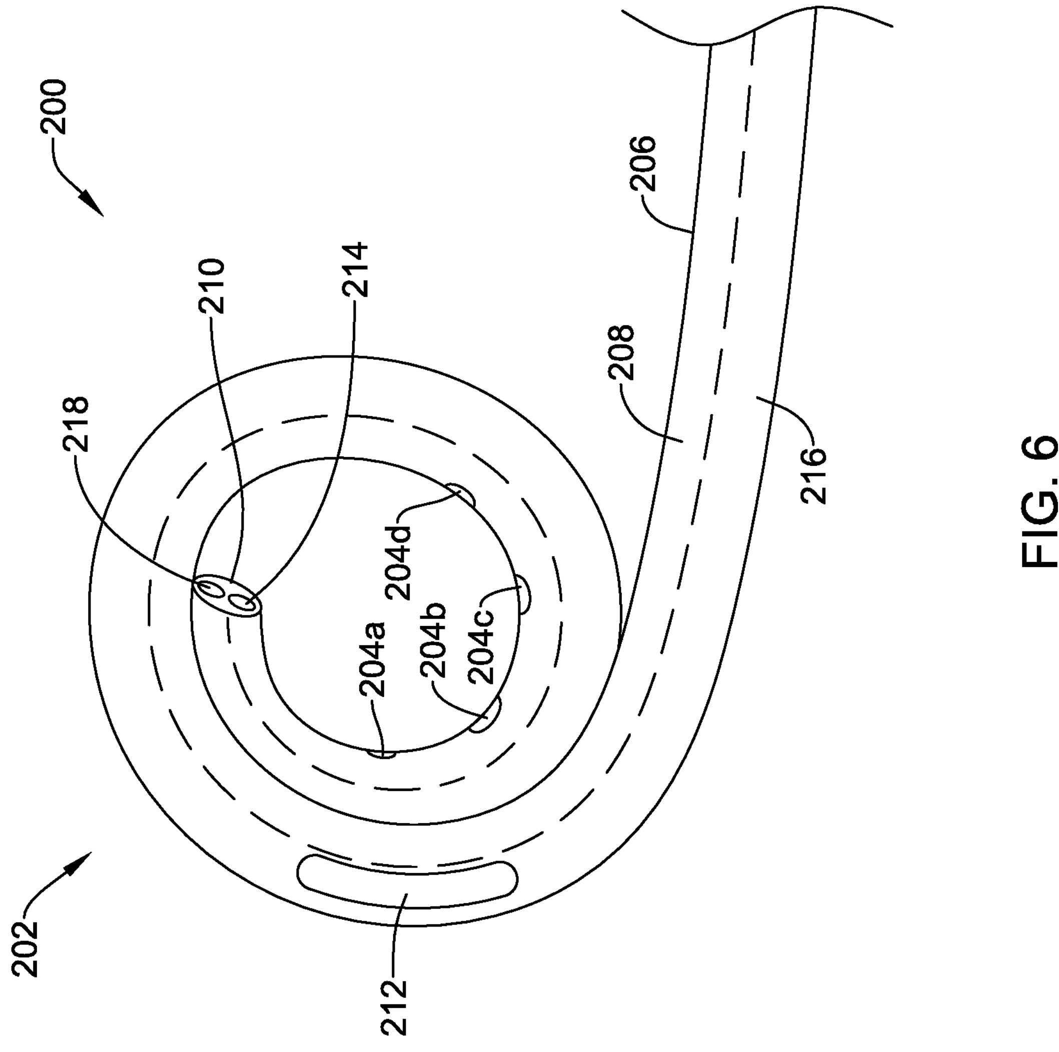
FIG. 6 is an illustrative pigtail catheter.

It is contemplated that prior to moving the medical implant 14 from the deployed configuration to the released configuration, it may be desirable to secure the medical implant 14 to the adjacent tissue. In some cases, the pigtail catheter 200 may be used to deliver an anchor that may be used to secure the medical implant 14 to one or more of the native valve leaflets 84. FIG. 6 is an enlarged perspective view of the distal end region 202 of the illustrative pigtail catheter 200. The pigtail catheter 200 includes a tubular elongate shaft 206 extending from a proximal end configured to remain outside the body to the distal end region 202. The elongate shaft 206 includes a first lumen 208 extending from the proximal end thereof to the distal end region 202. In some cases, the lumen 208 may terminate proximal to the distal end 210 of the elongate shaft 206 while in other cases, the lumen 208 may extend to the distal end 210 to define a distal opening 214. In some embodiments, the elongate shaft 206 may include a second lumen 216. In some cases, the second lumen 216 may terminate proximal to the distal end 210 of the elongate shaft 206 while in other cases, the lumen 208 may extend to the distal end 210 to define a distal opening 218. When so provided, the two or more lumens 208, 216 may be arranged in a side by side or collinear arrangement, in a coaxial or tube within a tube arrangement, or combinations thereof. It is further contemplated that when so provided, the two or more lumens 208, 216 may be fluidly isolated from one another.

In the absence of an external biasing force, or in a deployed configuration, the distal end region 202 is configured to assume a curved pigtail or J shape. It is contemplated that the distal end region 202 may have any degree of curvature desired including less than 360° or greater than 360°, as desired. The distal end region 202 may be biased into a generally linear or delivery configuration by for example, a guidewire or stiffening member slidably disposed within one or more of the lumens 208, 216 or a stiffer tube (such as, but not limited to an outer sheath 102) disposed over an outer surface of the pigtail catheter 200. These are just examples and are not intended to limit the pigtail catheter 200 to a particular configuration.

The pigtail catheter 200 includes a side port 212. While only a single side port 212 is illustrated, the pigtail catheter 200 may include more than one side port 212, as desired. In some embodiments, the first set of apertures 204 may be in fluid communication with a radiopaque fluid source and/or a contrast fluid source while the side port 212 may be configured to deploy an implantable anchor or fixation member from the second lumen 216 of the pigtail catheter 200 and into the body of a patient. For example, the implantable anchor member may be pushed out of the side port 212 and into a native leaflet 84 of the aortic valve 82 and the medical implant 14 using a stiff guidewire, or other pushing element, as will be described in more detail herein. The side port 212 may be positioned such that the pushing element exits perpendicular to the pigtail catheter 200.

In some cases, the first set of apertures 204 may be positioned on the elongate shaft 206 such that when the distal end region 202 of the pigtail catheter 200 is in the deployed configuration, the first set of apertures 204 are positioned or directed radially inwards relative to the curve of the distal end region 202 (or on the concave surface thereof). However, this is not required. In some cases, the first set of apertures 204 may be positioned on the elongate shaft 206 such that when the distal end region 202 of the pigtail catheter 200 is in the deployed configuration the first set of apertures 204 are positioned or directed radially outwards (not explicitly shown) relative to the curve of the distal end region 202 (or on the convex surface thereof). It is contemplated that the position of the first set of apertures 204 is not limited to the radially inward or outward surface of the distal end region 202. It is contemplated that the first set of apertures 204 may be positioned at any circumferential location about the elongate shaft 206, or combinations of circumferential locations, as desired.

In some cases, the side port 212 may be positioned on the elongate shaft 206 such that when the distal end region 202 of the pigtail catheter 200 is in the deployed configuration, the side port 212 is positioned or directed radially outwards relative to the curve of the distal end region 202 (or on the convex surface thereof). However, this is not required. In some cases, the side port 212 may be positioned on the elongate shaft 206 such that when the distal end region 202 of the pigtail catheter 200 is in the deployed configuration the side port 212 is positioned or directed radially inwards (not explicitly shown) relative to the curve of the distal end region 202 (or on the concave surface thereof). It is contemplated that the position of the side port 212 is not limited to the radially inward or outward surface of the distal end region 202. It is contemplated that the side port 212 may be positioned at any circumferential location about the elongate shaft 206, or combinations of circumferential locations, as desired.

Figure 7:
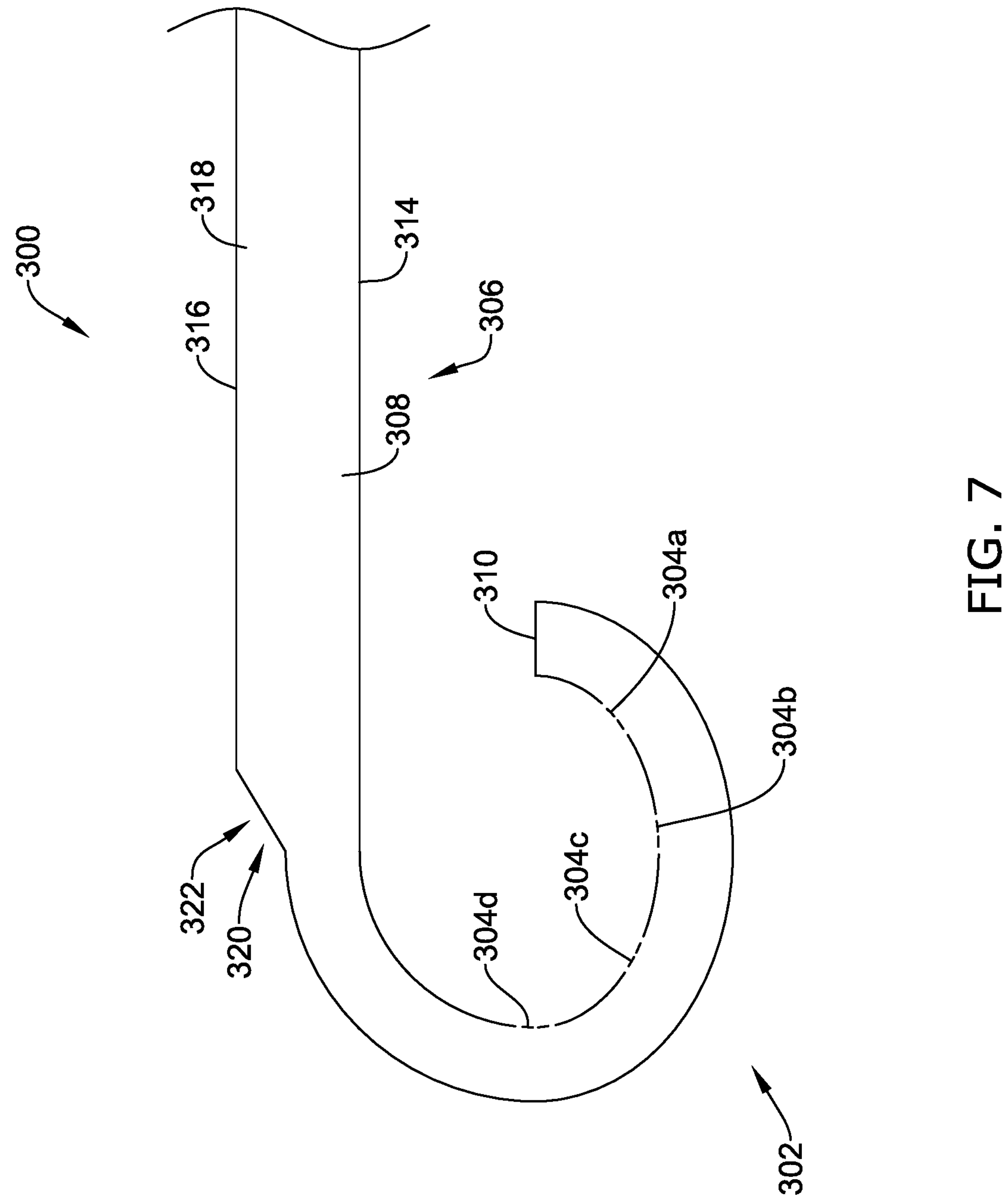
FIG. 7 is another illustrative pigtail catheter.

FIG. 7 is an enlarged partial side view of another illustrative pigtail catheter 300. The pigtail catheter 300 includes a tubular elongate shaft 306 extending from a proximal end configured to remain outside the body to the distal end region 302. The elongate shaft 306 includes at least a first lumen 308 configured to deliver a radiopaque fluid and/or a contrast fluid and a second lumen 318 configured to deliver an implantable radiopaque marker. The two or more lumens 308, 318 may be arranged in a side by side or collinear arrangement, in a coaxial or tube within a tube arrangement, or combinations thereof. The two or more lumens 308, 318 may be fluidly isolated from another The elongate shaft 306 may include a first portion 314 defining the first lumen 308 and a second portion 316 defining the second lumen 318. It is contemplated that the first and second portions 314, 316 need not have the same length as each other. In some embodiments, the elongate shaft 306 may be extruded as a single monolithic structure to form side-by-side lumens 308, 318. In other embodiments, the elongate shaft 306 may be formed by other suitable means, such as a first and a second separate extruded tubes arranged side-by-side and connected by adhesive, or the like.

The first lumen 308 may extend from the proximal end of the first portion 314 towards a distal end 310 thereof. In some cases, the first lumen 308 may terminate proximal to the distal end 310 of the first portion 314 while in other cases, the first lumen 308 may extend to the distal end 310 to define a distal opening (not explicitly shown). The second lumen 318 may extend from the proximal end of the second portion 316 towards a distal end 320 thereof. The second lumen 318 may extend to the distal end 320 to define a distal opening 322 (e.g., distally facing). However, this is not required. In some cases, the second lumen 318 may terminate proximal to the distal end 320. In such an instance, a side port may be provided to allow an implantable fixation member to be advanced through and exit the second lumen 318.

In the absence of an external biasing force, or in a deployed configuration, the distal end region 302 is configured to assume a curved pigtail or J shape. It is contemplated that the distal end region 302 may have any degree of curvature desired including less than 360° or greater than 360°, as desired. The distal end region 302 may be biased into a generally linear or delivery configuration by for example, a guidewire or stiffening member slidably disposed within the lumen 308 or a stiffer tube (such as, but not limited to an outer sheath) disposed over an outer surface of the pigtail catheter 300. These are just examples and are not intended to limit the pigtail catheter 300 to a particular configuration.

The first portion 314 includes a set of holes or apertures 304*a*, 304*b*, 304*c*, 304*d* (collectively, 304). The set of apertures 304 may include one, two, three, four, or more apertures, as desired. The set of apertures 304 may be in fluid communication with a radiopaque fluid source and/or a contrast fluid source. This may allow for the delivery of a radiopaque fluid and an implantable fixation member through separate lumens 308, 318, if so desired. As described herein, the second portion 316 may include a distal opening 322 through which an implantable fixation member is deployable. For example, the implantable fixation member may be pushed out of the distal opening 322 and into the native leaflet 84 of the aortic valve 82 and the medical implant 14 using a stiff guidewire, or other pushing element, as will be described in more detail herein.

In some cases, the set of apertures 304 may be positioned on the first portion 314 such that when the distal end region 302 of the pigtail catheter 300 is in the deployed configuration, the set of apertures 304 are positioned or directed radially inwards relative to the curve of the distal end region 302 (or on the concave surface thereof). However, this is not required. In some cases, the first set of apertures 304 may be positioned on the elongate shaft 306 such that when the distal end region 302 of the pigtail catheter 300 is in the deployed configuration the first set of apertures 304 are positioned or directed radially outwards (not explicitly shown) relative to the curve of the distal end region 302 (or on the convex surface thereof). It is contemplated that the position of the set of apertures 304 is not limited to the radially inward or outward surface of the distal end region 302. It is contemplated that the set of apertures 304 may be positioned at any circumferential location about the portion 314, or combinations of circumferential locations, as desired.

Returning to FIG. 5, to deploy an implantable anchor or fixation member, a delivery needle 250 may be advanced through the lumen 208 of the pigtail catheter 200. It should be noted that while delivery of the implantable fixation member is described with respect to the pigtail catheter 200 illustrated in FIG. 6, other pigtail catheters, such as but not limited, pigtail catheter 300, or other delivery devices or systems may be used, as desired. The delivery needle 250 may extend from a distal end 252 to a proximal end configured to remain outside the body. The distal end 252 of the delivery needle 250 may be angled or otherwise define a sharp tip configured to penetrate bodily tissues. A lumen 254 configured to receive the implantable fixation member and a push wire may extend from the distal end 252 to the proximal end of the delivery needle 250.

Figure 8:
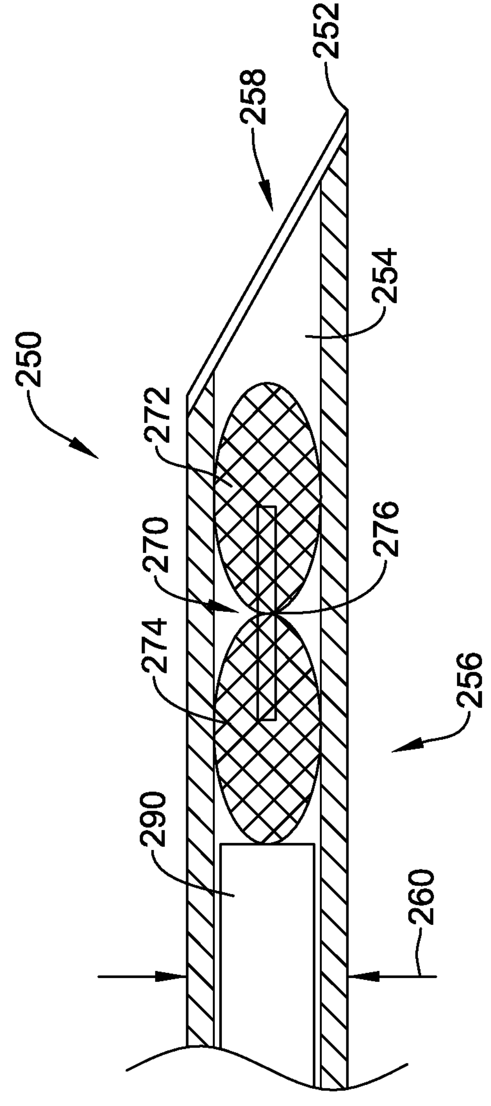
FIG. 8 is a partial cross-sectional view of a distal end region of an illustrative delivery needle with an implantable fixation member loaded into the lumen thereof.

Referring briefly to FIG. 8, which illustrates a partial cross-sectional view of a distal end region 256 of an illustrative delivery needle 250, an implantable fixation member 270 may be loaded into the lumen 254 thereof. The implantable fixation member 270 may be expandable from a collapsed delivery configuration (as shown in FIG. 8) to an expanded deployed configuration (see, for example, FIG. 11). The implantable fixation member 270 may be loaded into the lumen 254 of the delivery needle 250 through a distal opening 258 or a proximal opening (not explicitly shown), as desired. A push wire 290 may also be loaded into the lumen 254 of the delivery needle 250. It is contemplated that if the implantable fixation member 270 is loaded into the delivery needle 250 via a proximal opening, the push wire 290 may be used to push the implantable fixation member 270 through the lumen 254 to a location adjacent the distal end 252 of the implantable fixation member 270. If the implantable fixation member 270 is loaded via the distal opening 258, the push wire 290 may be loaded via the proximal opening (before or after the implantable fixation member 270) or via the distal opening 258 prior to the implantable fixation member 270. In some cases, the implantable fixation member 270 and the push wire 290 may be loaded into the delivery needle 250 prior to advancing the delivery needle through the pigtail catheter 200. In other cases, the implantable fixation member 270 and the push wire 290 may be loaded into the delivery needle 250 after the delivery needle has been advanced through the pigtail catheter.

The implantable fixation member 270 may include a first or distal expandable basket 272 and a second or proximal expandable basket 274. It is contemplated that the baskets 272, 274 may be formed from a shape memory or superelastic material, such as, but not limited to, nitinol, so that the baskets 272, 274 are self-expanding upon deployment. In other cases, the baskets 272, 274 may be connected to an actuation mechanism to move the baskets 272, 274 from the collapsed delivery configuration to the expanded deployed configuration. The baskets 272, 274 may be connected by an elongate connecting member 276. The baskets 272, 274 may expand in diameter in the absence of a radially compressing force (e.g., the inner surface of the delivery needle 250). The baskets 272, 274 may have a woven or braided structure similar to a stent. However, this is not required. In some cases, the baskets 272, 274 may be laser cut or any other collapsible structure. In the expanded form, the baskets 272, 274 may have a cross sectional dimension that is greater than an outer diameter 260 of the delivery needle 250. As will be described in more detail herein, this may help secure the implantable fixation member 270 in the desired location.

Returning to FIG. 5, once the medical implant 14 is in the "deployed" configuration, the distal end region 202 of the pigtail catheter 200 may be positioned near or adjacent to the at least one of the native valve leaflets 84. The pigtail catheter 200 is oriented such that the side port 212 is adjacent to the native valve leaflet 84. The delivery needle 250 may be advanced through the lumen 208 of the pigtail catheter 200, if it was not previously positioned. The delivery needle 250 may be distally advanced so that it exits the side port 212. In some cases, the delivery needle 250 may be formed from a shape memory or superelastic material, such as, but not limited to nitinol. The delivery needle 250 may be heat treated or set such that the "remembered" shape of the distal end region 256 of the delivery needle 250 is curved relative to a longitudinal axis of a proximal end region of the delivery needle. The distal end region 256 of the delivery needle 250 may be biased to a generally linear configuration within the lumen 208 of the pigtail catheter 200 to facilitate advancement therethrough. Once the distal end region 256 of the delivery needle 250 exits the pigtail catheter 200, the distal end region 256 may return to the curved "remembered" shape. This may help direct the delivery needle 250 towards the native valve leaflet 84. In other embodiments, the delivery needle 250 may be generally linear from a proximal end to the distal end 252 thereof.

Figure 9:
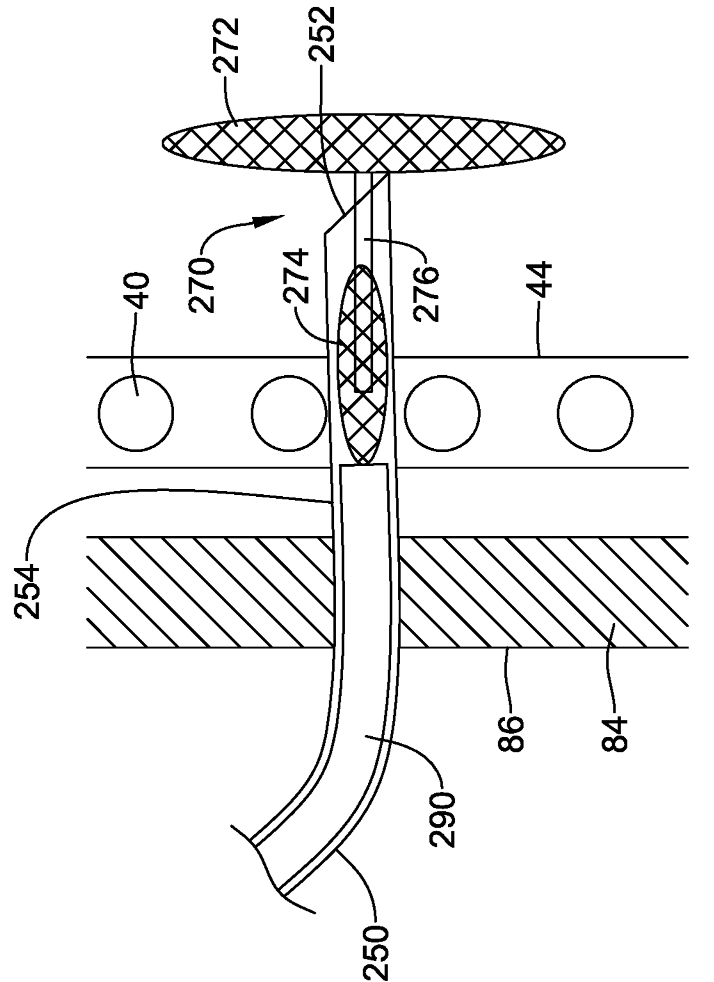
FIG. 9 illustrates the implantable fixation member of FIG. 8 in a partially deployed configuration.
Figure 10:
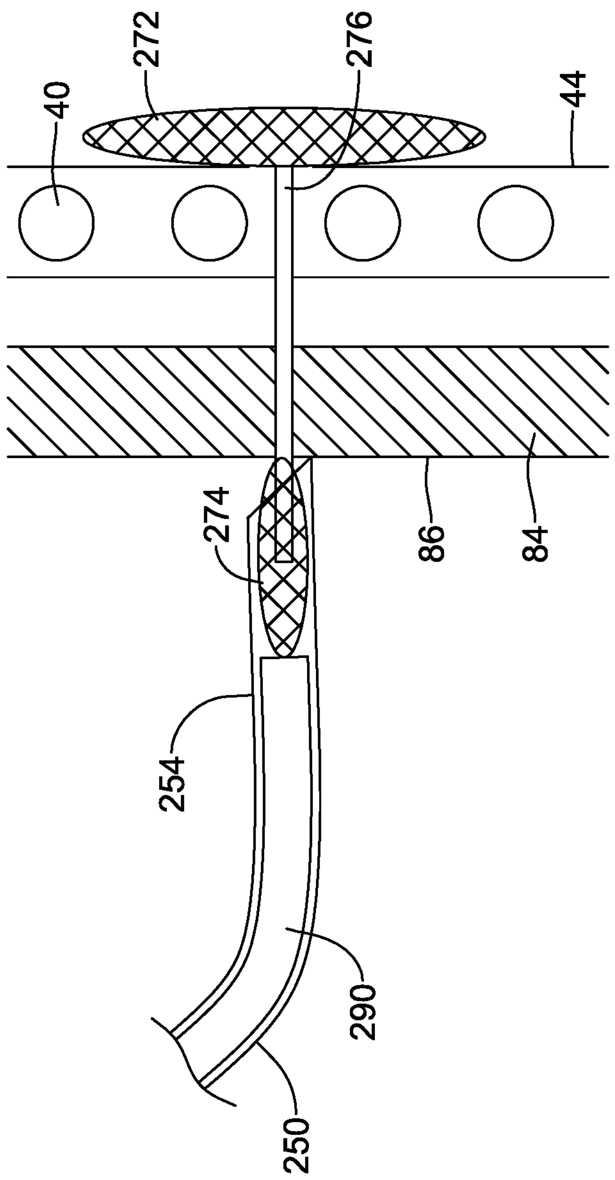
FIG. 10 illustrates the implantable fixation member of FIG. 8 in another partially deployed configuration.
Figure 11:
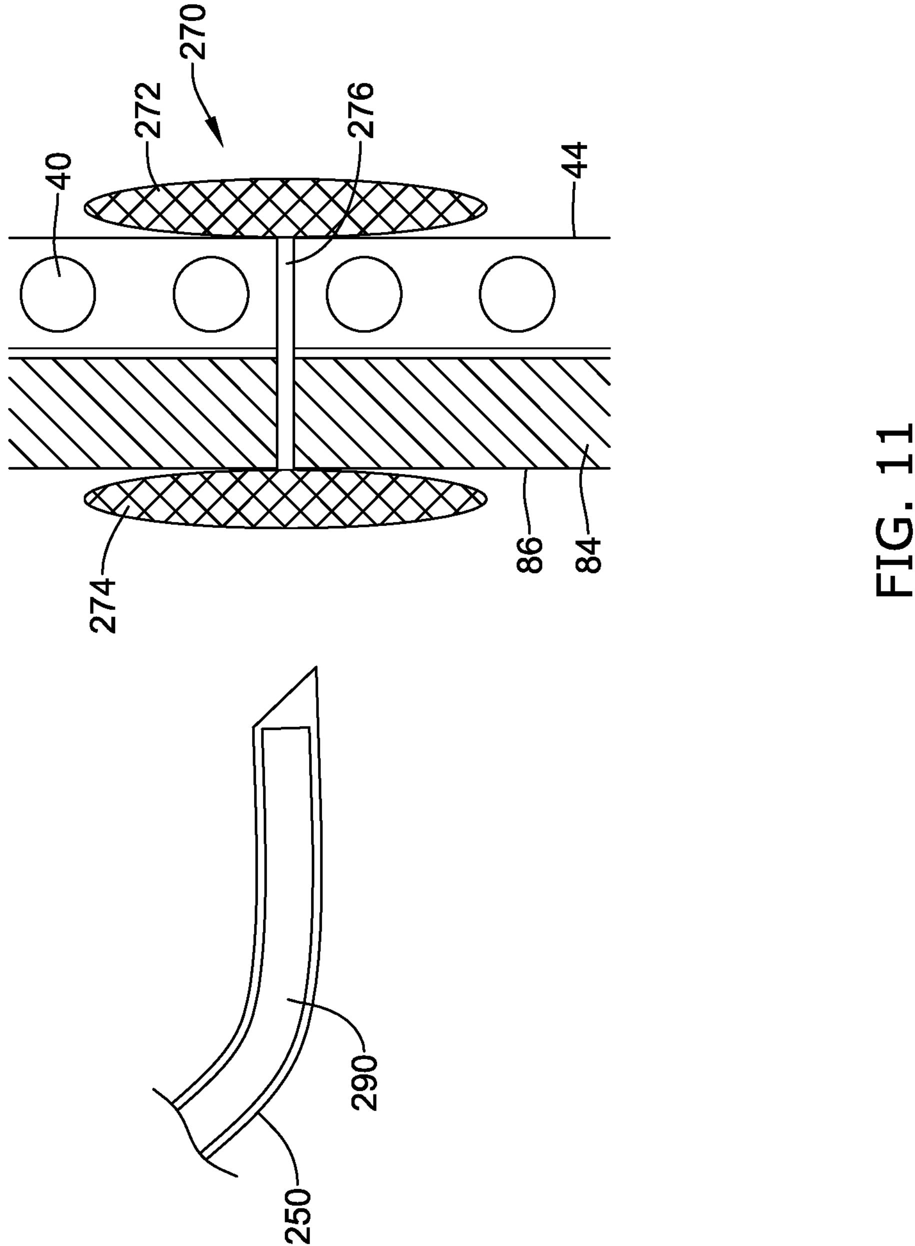
FIG. 11 illustrates the implantable fixation member of FIG. 8 in a deployed configuration.

The deployment of the implantable fixation member 270 is described with respect to FIGS. 9-11. FIGS. 9-11 illustrate an enlarged view of region A of FIG. 5, with the implantable fixation member 270 in various stages of deployment. The distal end 252 of the delivery needle 250 may be pushed through the native valve leaflet 84 and through the anchor member 40 and/or seal 44 of the medical implant 14. Once the distal end 252 is disposed within a lumen of the medical implant 14, the push wire 290 may be distally actuated to push the implantable fixation member 270 out of the lumen 254 of the delivery needle 250, until the distal basket 272 is deployed from the delivery needle 250, as shown in FIG. 9. The delivery of the implantable fixation member 270 may be done under fluoroscopy to allow for precise deployment of the implantable fixation member 270. In some cases, the implantable fixation member 270, the delivery needle 250, and/or the push wire 290 may include one or more radiopaque markers to facilitate deployment of the implantable fixation member 270. As the distal basket 272 exits the lumen 254, the distal basket 272 may resume its expanded configuration. The expanded shape of the distal basket 272 may be greater than the outer diameter of the delivery needle 250 such that the distal basket 272 is precluded from passing through the aperture in the anchor member 40 and/or seal 44 of the medical implant 14 formed by the penetrating delivery needle 250.

Once the distal basket 272 has been deployed, the delivery needle 250 may be proximally retracted through a thickness a sidewall of the anchor member 40 and/or seal 44 of the medical implant 14 and a thickness of the native valve leaflet 84 until the distal end 252 is adjacent to a first side 86 of the native valve leaflet 84, as shown in FIG. 10. As used herein, the first side 86 of the native valve leaflet 84 is the side of the leaflet 84 that is not in contact with the medical implant 14. Frictional engagement between the proximal basket 274 and the inner surface of the delivery needle 250 may maintain the proximal basket 274 within the lumen 254 as the delivery needle 250 is proximally retracted. In some cases, proximal retraction of the delivery needle 250 may bring the distal basket 272 into engagement with an inner surface of the anchor member 40 and/or seal 44 of the medical implant 14.

Once the distal end 252 is disposed on the first side 86 of the native valve leaflet 84, the push wire 290 may be distally actuated to push the implantable fixation member 270 out of the lumen 254 of the delivery needle 250, until the proximal basket 274 is deployed from the delivery needle 250, as shown in FIG. 11. As the proximal basket 274 exits the lumen 254, the proximal basket 274 may resume its expanded configuration. The expanded shape of the proximal basket 274 may be greater than the outer diameter of the delivery needle 250 such that the proximal basket 274 is precluded from passing through the aperture in the native valve leaflet 84 formed by the penetrating delivery needle 250. It is contemplated that the elongate connecting member 276 may have a length that is approximately equal to a combined thickness of a sidewall of the anchor member 40 and/or seal 44 of the medical implant 14 and the native valve leaflet 84. In other cases, the elongate connecting member 276 may have a length that is less than to a combined thickness of a sidewall of the anchor member 40 and/or seal 44 of the medical implant 14 and the native valve leaflet 84. This may cause the implantable fixation member 270 to exert a compressive force on the anchor member 40 and/or seal 44 of the medical implant 14 and the native valve leaflet 84. In yet other cases, the elongate connecting member 276 may have a length that is greater than to a combined thickness of a sidewall of the anchor member 40 and/or seal 44 of the medical implant 14 and the native valve leaflet 84. This may allow for some relative movement between the implantable fixation member 270 and the anchor member 40 and/or seal 44 of the medical implant 14 and the native valve leaflet 84.

The method to deliver an implantable fixation member 270 may be repeated as many times as desired to secure the medical implant 14 within the body. It is contemplated that an implantable fixation member 270 may be secured through each of the native valve leaflets 84. However, this is not required. The medical implant 14 may be secured with any number of implantable fixation members 270 desired, including but not limited to, one, two, three, four, five, six, or more. In some cases, a plurality of implantable fixation members 270 may be loaded into the lumen 254 the delivery needle 250 such that the delivery needle 250 does not need to be removed from the body to deliver more than one implantable fixation member 270. In other cases, the delivery needle 250 may be removed after the delivery of each implantable fixation member 270 and reloaded with an additional implantable fixation member 270.

Figure 12:
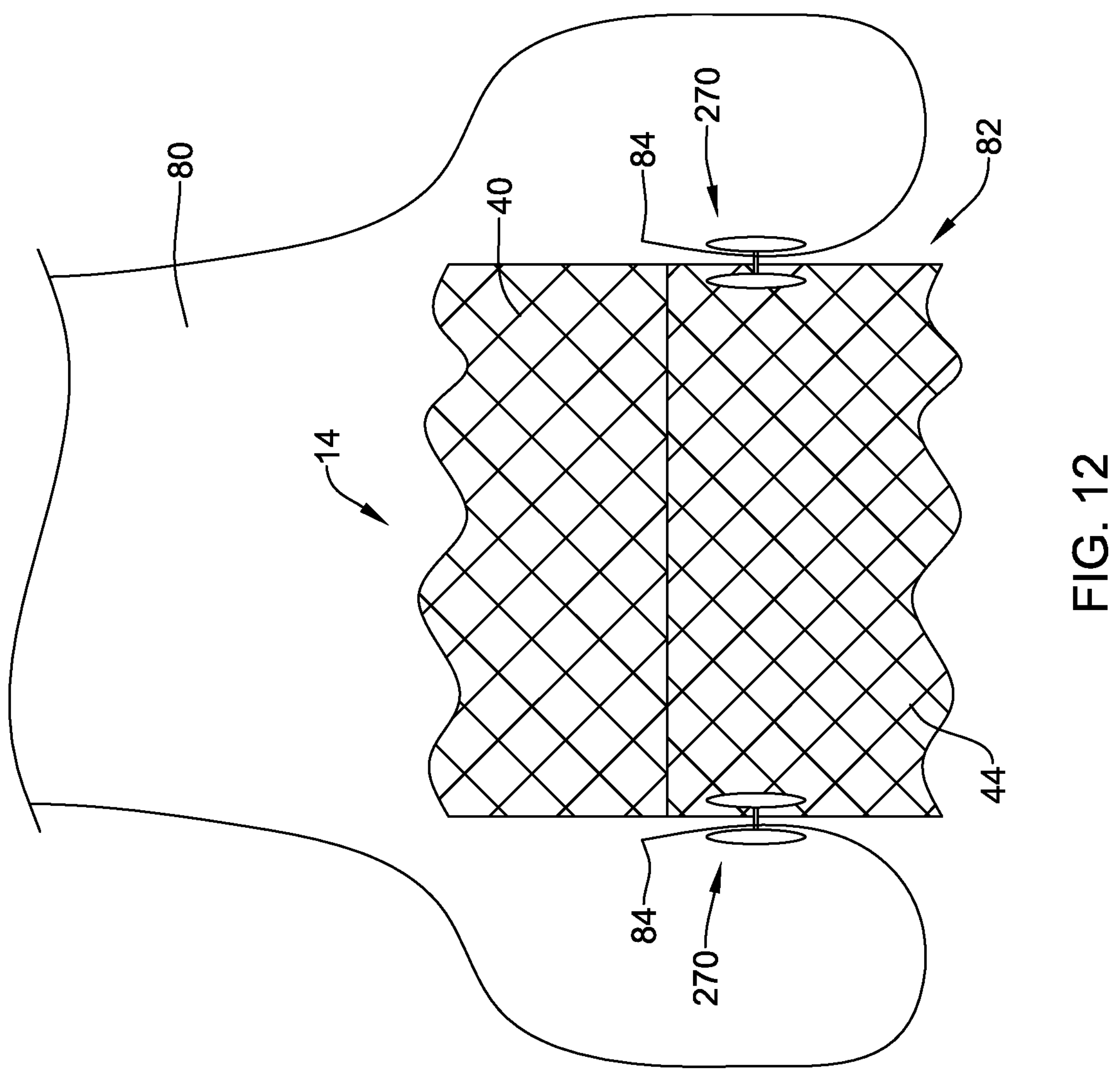
FIG. 12 is a schematic view of the illustrative implant of FIG. 1 in a deployed configuration within the body with a plurality of illustrative fixation members.

Once the implantable fixation members 270 have been deployed (e.g., secured to the medical implant 14 and the native tissue), the clinician may test the stability of the medical implant 14. If the medical implant 14 is not stable or considered to be at risk of dislodgment, the clinician may deliver and deploy one or more additional implantable fixation members 270 between the medical implant 14 and native tissue (e.g., leaflet 84). Once the medical implant 14 is stable, the clinician may then move the medical implant 14 from the "deployed" configuration to the "released" configuration, as shown in FIG. 12.

After the medical implant 14 is released, the delivery system 12 and any other components (including but not limited to the pigtail catheters 200, guidewires, etc.) may be removed, if they have not already been removed.

Figure 13B:
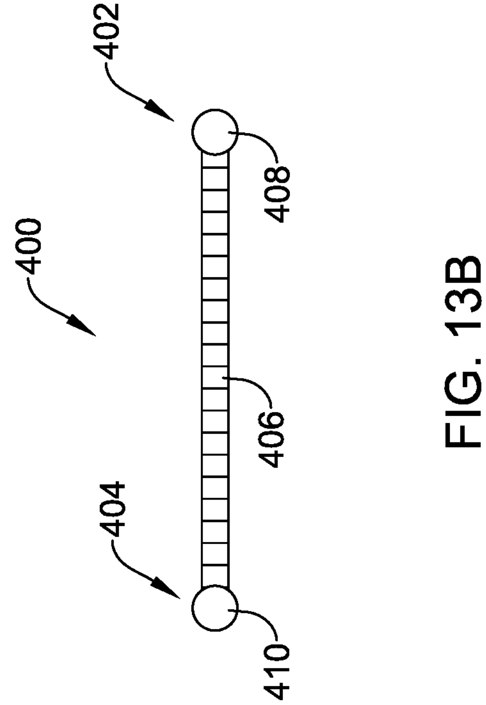
FIG. 13B is a schematic side view of the illustrative fixation member of FIG. 13A in a collapsed configuration.
Figure 13A:
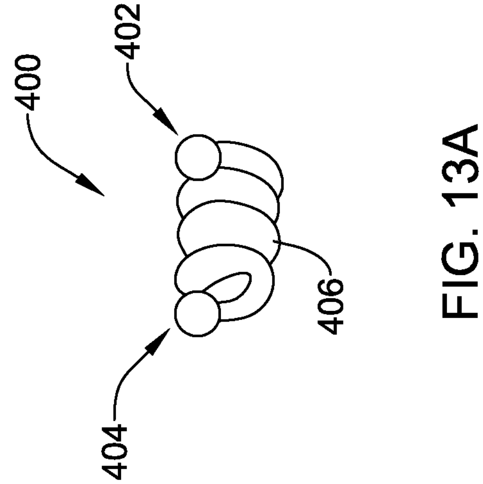
FIG. 13A is a schematic side view of another illustrative implantable fixation member in an expanded configuration.

FIG. 13A is a schematic side view of another illustrative implantable anchor or fixation member 400 for securing a medical implant 14 to body tissue (e.g., native valve leaflets 84) in a deployed or expanded configuration. FIG. 13B illustrates the implantable fixation member 400 in a second, or radially collapsed, delivery configuration. In some cases, the implantable fixation member 400 may be elongated (e.g., longer) in the delivery configuration than the expanded deployed configuration, although this is not required. In the expanded configuration, the implantable fixation member 400 may be a helical winding or have a generally spring-like shape extending from a proximal end 404 to a distal end 402. The pitch (e.g., the distance from the center of one coil to the center of the adjacent coil), the angle of the winding, and/or spacing of adjacent winding may be varied to achieve a desired effect. For example, an implantable fixation member 400 having adjacent windings that contact one another in the expanded configuration may exert a greater compressive force on the medical implant and the native tissue when the implantable fixation member 400 is deployed than an implantable fixation member 400 having some space between adjacent windings.

It is contemplated that the implantable fixation member 400 may be formed from a shape memory or superelastic material, such as, but not limited to nitinol. The implantable fixation member 400 may be heat treated or set such that the "remembered" shape of the implantable fixation member 400 is the coiled expanded configuration of FIG. 13A. The implantable fixation member 400 may be biased into a generally linear configuration, as shown in FIG. 13B, within a lumen of a delivery needle (e.g., delivery needle 250) to facilitate delivery of the implantable fixation member 400. As the implantable fixation member 400 exits the delivery needle, the implantable fixation member 400 may return to the coiled "remembered" shape. The implantable fixation member 400 may include one or more retaining features 408, 410 positioned at the distal end 402 and the proximal end 404 thereof In some cases, only one of the illustrated retaining features 408, 410 or none of the retaining features may be present. In some cases, the retaining features 408, 410 may be atraumatic. The retaining features 408, 410 may have a generally spherical or bulbous shape having a cross-sectional dimension that is greater than a cross-sectional dimension of the filament 406. The retaining features 408, 410 may help maintain the implantable fixation member 400 in the desired position once the implantable fixation member 400 has been deployed. It is contemplated that the retaining features 408, 410 may take other shapes as desired.

The implantable fixation member 400 may be deployed in a similar manner to the implantable fixation member 270 described herein. For example, the implantable fixation member 400 may be loaded into a delivery needle, such as, but not limited to the delivery needle 250 described herein, which is advanced through a pigtail catheter, such as, but not limited to, the pigtail catheters 200, 300 described herein. The distal end of the delivery needle may be pushed through the native valve leaflet and through a sidewall the anchor member and/or seal of the medical implant. Once the distal end is disposed within a lumen of the medical implant, a push wire, such as, but not limited to, the push wire 290 described herein may be distally actuated to push a distal end region of the implantable fixation member 400 out of the lumen of the delivery needle, until a portion of the implantable fixation member 400 is deployed from the delivery needle. The delivery of the implantable fixation member implantable fixation member 400 may be done under fluoroscopy to allow for precise deployment of the implantable fixation member implantable fixation member 400. In some cases, the implantable fixation member implantable fixation member 400, the delivery needle, and/or the push wire may include one or more radiopaque markers to facilitate deployment of the implantable fixation member 400. As the distal end 402 of the implantable fixation member 400 exits the lumen, the deployed portion of the implantable fixation member 400 may resume its expanded configuration. The expanded shape of the implantable fixation member 400 may be greater than the outer diameter of the delivery needle such that the implantable fixation member 400 is precluded from passing through the aperture in the formed by the penetrating delivery needle. In some cases, the implantable fixation member 400 may be distally advanced until at least one winding has been deployed. However, this is not required. It is contemplated that less than one full winding may be deployed within the lumen of the medial device, is so desired.

Once the distal end region of the implantable fixation member 400 has been at least partially deployed (or expanded), the delivery needle may be proximally retracted through a thickness of a side wall of the anchor member and/or seal of the medical implant and a thickness of the native valve leaflet until the distal end of the delivery needle is adjacent to a first side of the native valve leaflet. As used herein, the first side of the native valve leaflet is the side of the leaflet that is not in contact with the medical implant. Frictional engagement between the proximal end region of the implantable fixation member 400 and the inner surface of the delivery needle may maintain the proximal end region of the implantable fixation member 400 within the lumen as the delivery needle is proximally retracted. In some cases, proximal retraction of the delivery needle may bring the distal end region of the implantable fixation member 400 into engagement with an inner surface of the anchor member and/or seal of the medical implant.

Once the distal end of the delivery needle is disposed on the first side of the native valve leaflet, the push wire may be distally actuated to push the implantable fixation member 400 out of the lumen of the delivery needle, until the remainder of the implantable fixation member 400 is deployed from the delivery needle. As the proximal end region of the implantable fixation member 400 exits the lumen, the proximal end region of the implantable fixation member 400 may resume its expanded configuration. The expanded shape of the proximal end region of the implantable fixation member 400 may be greater than the outer diameter of the delivery needle such that the proximal end region of the implantable fixation member 400 is precluded from passing through the aperture in the native valve leaflet formed by the penetrating delivery needle. It is contemplated that the portion of the implantable fixation member 400 passing through the thickness of a sidewall of the anchor member and/or seal of the medical implant and the native valve leaflet may have a generally linear configuration or may have a curved configuration that is intermediary to the expanded configuration of FIG. 13A and the delivery configuration of FIG. 13B.

The method to deliver an implantable fixation member 400 may be repeated as many times as desired to secure the medical implant within the body. It is contemplated that an implantable fixation member 400 may be secured through each of the native valve leaflets. However, this is not required. The medical implant 14 may be secured with any number of implantable fixation member 400 desired, including but not limited to, one, two, three, four, five, six, or more. In some cases, a plurality of implantable fixation member 400 may be loaded into the lumen the delivery needle such that the delivery needle does not need to be removed from the body to deliver more than one implantable fixation member 400. In other cases, the delivery needle may be removed after the delivery of each implantable fixation member 400 and reloaded with an additional implantable fixation member 400.

Once the implantable fixation member 400 have been deployed (e.g., secured to the medical implant and the native tissue), the clinician may test the stability of the medical implant. If the medical implant is not stable or considered to be at risk of dislodgment, the clinician may deliver and deploy one or more additional implantable fixation member 400 between the medical implant and native tissue (e.g., leaflet). Once the medical implant is stable, the clinician may then move the medical implant 14 from the "deployed" configuration to the "released" configuration. After the medical implant is released, the delivery system and any other components (including but not limited to the pigtail catheters, guidewires, etc.) may be removed, if they have not already been removed.

Figure 14:
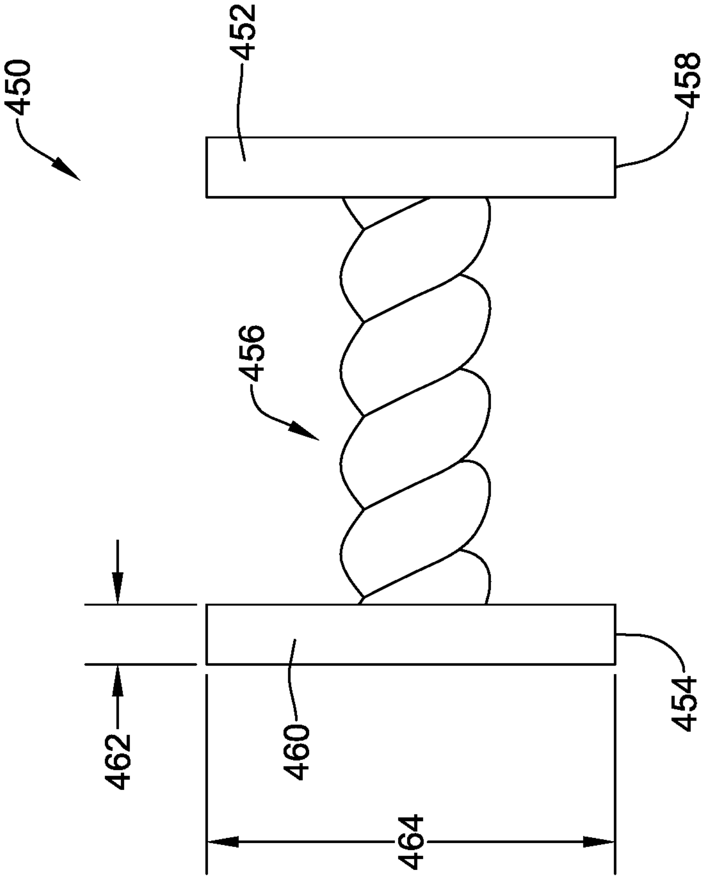
FIG. 14 is a schematic side view of another illustrative implantable fixation member in an expanded configuration.

FIG. 14 is a schematic side view of another illustrative implantable anchor or fixation member 450 for securing a medical implant to body tissue (e.g., native valve leaflets) in a deployed or expanded configuration. While not explicitly shown, the implantable fixation member 450 may be radially collapsed to a delivery configuration. In some cases, the implantable fixation member 450 may be elongated (e.g., longer) in the delivery configuration than the expanded deployed configuration, although this is not required. In the expanded configuration, the implantable fixation member 450 may have a generally spool-like or "I" shape extending from a proximal end 454 to a distal end 452. The implantable fixation member 450 may include retaining features 458, 460 positioned at the distal end 452 and the proximal end 454 thereof. The proximal end 454 and the distal end 452 may be interconnected with an elastic coil 456 extending therebetween. In some cases, only one of the illustrated retaining features 458, 460 or none of the retaining features 458, 460 may be present. In some cases, the retaining features 458, 460 may be atraumatic. The retaining features 458, 460 may have a generally planar three-dimensional shape having a narrow thickness 462 relative to a height 464 thereof. Some illustrative cross-sectional of the retaining features 458, 460 may include, but are not limited to, rectangular, circular, polygonal, ovoid, etc. The retaining features 458, 460 may have having a height 464 or another cross-sectional dimension that is greater than a cross-sectional dimension of the elastic coil 456. The retaining features 458, 460 may help maintain the implantable fixation member 450 in the desired position once the implantable fixation member 450 has been deployed. It is contemplated that the retaining features 458, 460 may take other shapes as desired. The interconnecting elastic coil 456 may be formed from an elastic material that may be stretched to span a combined thickness of the native valve leaflet and the medical implant side wall.

It is contemplated that the implantable fixation member 450 may be formed, at least in part, from a shape memory or superelastic material, such as, but not limited to nitinol. The implantable fixation member 450 may be heat treated or set such that the "remembered" shape of the implantable fixation member 450 is the expanded configuration of FIG. 14. The implantable fixation member 450 may be biased into a radially compress configuration within a lumen of a delivery needle (e.g., delivery needle 250) to facilitate delivery of the implantable fixation member 450. As the implantable fixation member 450 exits the delivery needle, the implantable fixation member 450 may return to the expanded "remembered" shape.

The implantable fixation member 450 may be deployed in a similar manner to the implantable fixation member 270 described herein. For example, the implantable fixation member 450 may be loaded into a delivery needle, such as, but not limited to the delivery needle 250 described herein, which is advanced through a pigtail catheter, such as, but not limited to, the pigtail catheters 200, 300 described herein. The distal end of the delivery needle may be pushed through the native valve leaflet and through a sidewall of the anchor member and/or seal of the medical implant. Once the distal end is disposed within a lumen of the medical implant, a push wire, such as, but not limited to, the push wire 290 described herein may be distally actuated to push the implantable fixation member 450 out of the lumen of the delivery needle, until the distal retaining feature 458 of the implantable fixation member 450 is deployed from the delivery needle. The delivery of the implantable fixation member implantable fixation member 450 may be done under fluoroscopy to allow for precise deployment of the implantable fixation member implantable fixation member 450. In some cases, the implantable fixation member implantable fixation member 450, the delivery needle, and/or the push wire may include one or more radiopaque markers to facilitate deployment of the implantable fixation member 450. As distal retaining feature 458 of the implantable fixation member 450 exits the lumen, the deployed portion of the implantable fixation member 450 may resume its expanded configuration. The expanded shape of the implantable fixation member 450 may be greater than the outer diameter of the delivery needle such that the implantable fixation member 450 is precluded from passing through the aperture in the formed by the penetrating delivery needle.

Once the distal retaining feature 458 of the implantable fixation member 450 has been deployed (or expanded), the delivery needle may be proximally retracted through a thickness of the anchor member and/or seal of the medical implant and a thickness of the native valve leaflet until the distal end of the delivery needle is adjacent to a first side of the native valve leaflet. As used herein, the first side of the native valve leaflet is the side of the leaflet that is not in contact with the medical implant. Frictional engagement between the proximal retaining feature 460 of the implantable fixation member 450 and the inner surface of the delivery needle may maintain the proximal end region of the implantable fixation member 450 within the lumen as the delivery needle is proximally retracted. In some cases, proximal retraction of the delivery needle may bring the distal retaining feature 458 of the implantable fixation member 450 into engagement with an inner surface of the anchor member and/or seal of the medical implant.

Once the distal end of the delivery needle is disposed on the first side of the native valve leaflet, the push wire may be distally actuated to push the implantable fixation member 450 out of the lumen of the delivery needle, until the remainder of the implantable fixation member 450 is deployed from the delivery needle. As the proximal retaining feature 460 of the implantable fixation member 450 exits the lumen, the proximal retaining feature 460 of the implantable fixation member 450 may resume its expanded configuration. The expanded shape of the proximal retaining feature 460 of the implantable fixation member 450 may be greater than the outer diameter of the delivery needle such that the proximal end region of the implantable fixation member 450 is precluded from passing through the aperture in the native valve leaflet formed by the penetrating delivery needle. It is contemplated that the interconnecting elastic coil 456 may have a length that is approximately equal to a combined thickness of a sidewall of the anchor member and/or seal of the medical implant and the native valve leaflet. In other cases, the interconnecting elastic coil 456 may have a length that is less than to a combined thickness of a sidewall of the anchor member and/or seal of the medical implant 14 and the native valve leaflet. This may cause the implantable fixation member 450 to exert a compressive force on the anchor member and/or seal of the medical implant and the native valve leaflet. In yet other cases, the interconnecting elastic coil 456 may have a length that is greater than to a combined thickness of a sidewall of the anchor member and/or seal of the medical implant and the native valve leaflet. This may allow for some relative movement between the implantable fixation member 450 and the anchor member and/or seal of the medical implant and the native valve leaflet.

The method to deliver an implantable fixation member 450 may be repeated as many times as desired to secure the medical implant within the body. It is contemplated that an implantable fixation member 450 may be secured through each of the native valve leaflets. However, this is not required. The medical implant 14 may be secured with any number of implantable fixation member 450 desired, including but not limited to, one, two, three, four, five, six, or more. In some cases, a plurality of implantable fixation member 450 may be loaded into the lumen the delivery needle such that the delivery needle does not need to be removed from the body to deliver more than one implantable fixation member 450. In other cases, the delivery needle may be removed after the delivery of each implantable fixation member 450 and reloaded with an additional implantable fixation member 450.

Once the implantable fixation member 450 have been deployed (e.g., secured to the medical implant and the native tissue), the clinician may test the stability of the medical implant. If the medical implant is not stable or considered to be at risk of dislodgment, the clinician may deliver and deploy one or more additional implantable fixation member 450 between the medical implant and native tissue (e.g., leaflet). Once the medical implant is stable, the clinician may then move the medical implant 14 from the "deployed" configuration to the "released" configuration. After the medical implant is released, the delivery system and any other components (including but not limited to the pigtail catheters, guidewires, etc.) may be removed, if they have not already been removed.

Figure 15B:
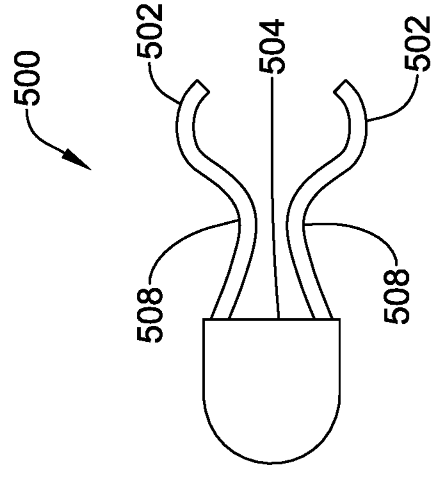
FIG. 15B is a schematic side view of the illustrative fixation member of FIG. 13A in a collapsed configuration.
Figure 15C:
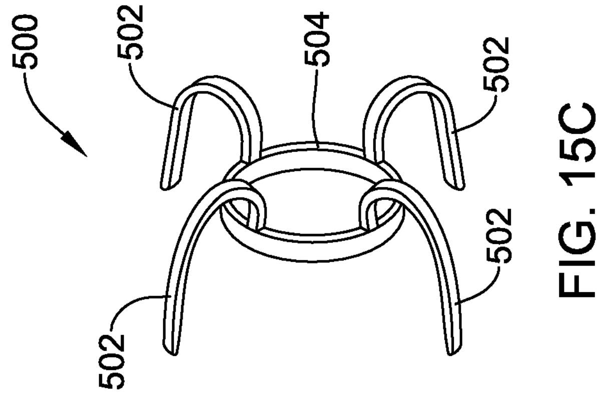
FIG. 15C is a side view of an alternative configuration of the illustrative implantable fixation member of FIG. 15A.
Figure 15A:
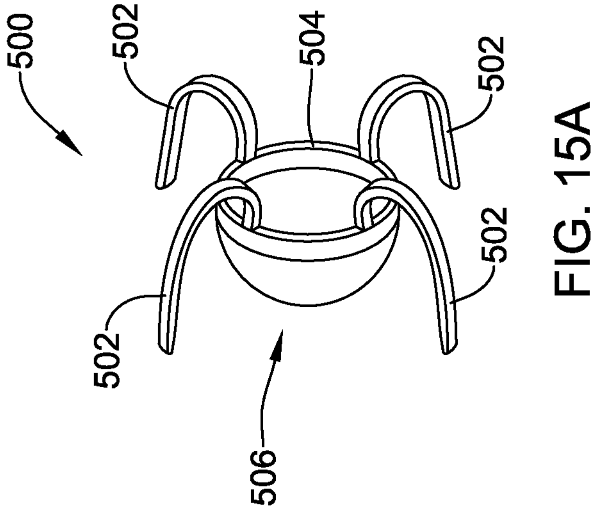
FIG. 15A is a schematic side view of another illustrative implantable fixation member in an expanded configuration.

FIG. 15A is a schematic perspective view of another illustrative implantable anchor or fixation member 500 for securing a medical implant to body tissue (e.g., native valve leaflets) in a deployed or expanded configuration. FIG. 15B illustrates a schematic side view of the implantable fixation member 500 in a second, or radially collapsed, delivery configuration. In some cases, the implantable fixation member 500 may be elongated (e.g., longer) in the delivery configuration than the expanded deployed configuration, although this is not required. The implantable fixation member 500 may include one or more hooks or tines 502 configured to anchor to the medical implant. In some cases, when implanted, the tines 502 may penetrate the medical implant and extend into the native valve leaflet, although this is not required. While the implantable fixation member 500 is illustrated as including four tines 502, it is contemplated that the implantable fixation member 500 may include any number of tines 502 such as but not limited to, one, two, three, four, or more. The tines 502 may be interconnected through a ring 504.

The implantable fixation member 500 may be formed from nitinol or other shape memory material which allows the tines 502 to be biased into a straightened configuration (as illustrated in FIG. 15B) for advancing the implantable fixation member 500 to the implant location. The tines 502 may be maintained in the straightened configuration during advancement using, for example, a delivery needle and allowed to assume the curved shape shown in FIG. 15A when the implantable fixation member 500 is in the desired location. In other words, the tines 502 may be advanced into the native valve leaflet and/or the medical implant in a straight configuration and when implant location is confirmed, the delivery needle removed to allow the tines 502 to bend and attach the implantable fixation member 500 to the medical implant and/or tissue wall.

In some cases, the implantable fixation member 500 may further include an atraumatic proximal end bumper 506. The bumper 506 may be formed from a same material as the ring 504 and/or tines 502 or a different material, as desired. The bumper 506 may have a generally solid cross-section to provide a surface for a push wire to exert a distal pushing force upon. While the bumper 506 is illustrated as having a generally hemispherical shape, the bumper 506 may take any shape desired. In some embodiments, the implantable fixation member 500 may not include the bumper 506, as illustrated in FIG. 15C.

The implantable fixation member 500 may be deployed in a similar manner to the implantable fixation member 270 described herein. For example, the implantable fixation member 500 may be loaded into a delivery needle, such as, but not limited to the delivery needle 250 described herein, which is advanced through a pigtail catheter, such as, but not limited to, the pigtail catheters 200, 300 described herein. In contrast with the delivery of the implantable fixation member 270, to deliver the implantable fixation member 500, the delivery needle may not be delivered through the native valve leaflet or the medical implant.

Figure 16:
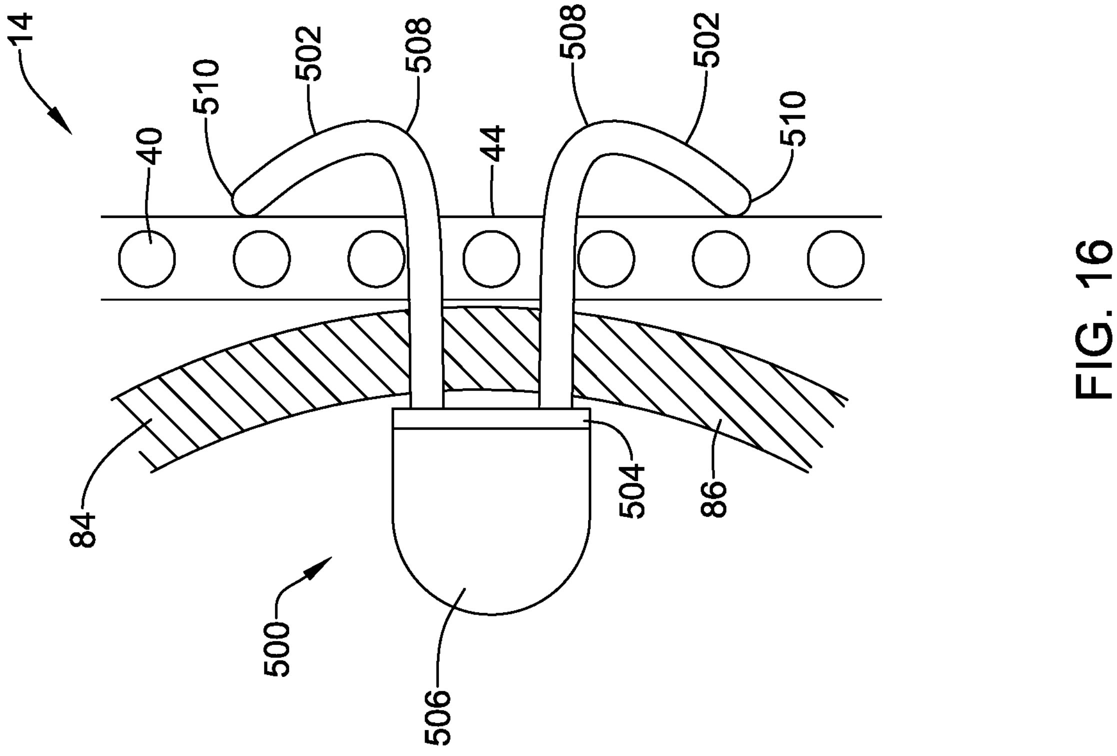
FIG. 16 illustrates the implantable fixation member of FIG. 15A in a deployed configuration.

For example, the delivery needle may be advanced to a first side of the native valve leaflet. As used herein, the first side of the native valve leaflet is the side of the leaflet that is not in contact with the medical implant. Once the distal end of the delivery needle is adjacent to the first side of the native valve leaflet, push wire, such as, but not limited to, the push wire 290 described herein may be distally actuated to push the implantable fixation member 500 out of the lumen of the delivery needle. As the implantable fixation member 500 is distally advanced, the tines 502 may first penetrate and pass through the native valve leaflet and then the anchor member and/or seal of the medical implant. The tines 502 may be maintained in their generally straightened configuration until the predefined bend portion 508 exits the lumen of the delivery needle and/or extends through the tissue/implant wall. Once a constraining force is released from the predefined bend portion 508, the implantable fixation member 500 may assume its expanded deployed configuration. It is contemplated that the implantable fixation member 500 may be sized such that the ring 504 contacts the first side 86 of the valve leaflet 84, as shown in FIG. 16, which illustrates the implantable fixation member 500 in a deployed configuration and engaged with the leaflet 84 and the medical implant 14. The tips or ends 510 of the tines 502 may bend back and contact the inner surface of the anchor member 40 and/or seal 44 of the medical implant 14. This may prevent the implantable fixation member 500 from becoming disengaged from the medical implant and/or the native valve leaflet 84.

The delivery of the implantable fixation member implantable fixation member 500 may be done under fluoroscopy to allow for precise deployment of the implantable fixation member implantable fixation member 500. In some cases, the implantable fixation member implantable fixation member 500, the delivery needle, and/or the push wire may include one or more radiopaque markers to facilitate deployment of the implantable fixation member 500.

The method to deliver an implantable fixation member 500 may be repeated as many times as desired to secure the medical implant within the body. It is contemplated that an implantable fixation member 500 may be secured through each of the native valve leaflets. However, this is not required. The medical implant 14 may be secured with any number of implantable fixation member 500 desired, including but not limited to, one, two, three, four, five, six, or more. In some cases, a plurality of implantable fixation member 500 may be loaded into the lumen the delivery needle such that the delivery needle does not need to be removed from the body to deliver more than one implantable fixation member 500. In other cases, the delivery needle may be removed after the delivery of each implantable fixation member 500 and reloaded with an additional implantable fixation member 500.

Once the implantable fixation member 500 have been deployed (e.g., secured to the medical implant and the native tissue), the clinician may test the stability of the medical implant. If the medical implant is not stable or considered to be at risk of dislodgment, the clinician may deliver and deploy one or more additional implantable fixation member 500 between the medical implant and native tissue (e.g., leaflet). Once the medical implant is stable, the clinician may then move the medical implant 14 from the "deployed" configuration to the "released" configuration. After the medical implant is released, the delivery system and any other components (including but not limited to the pigtail catheters, guidewires, etc.) may be removed, if they have not already been removed.

Figure 17:
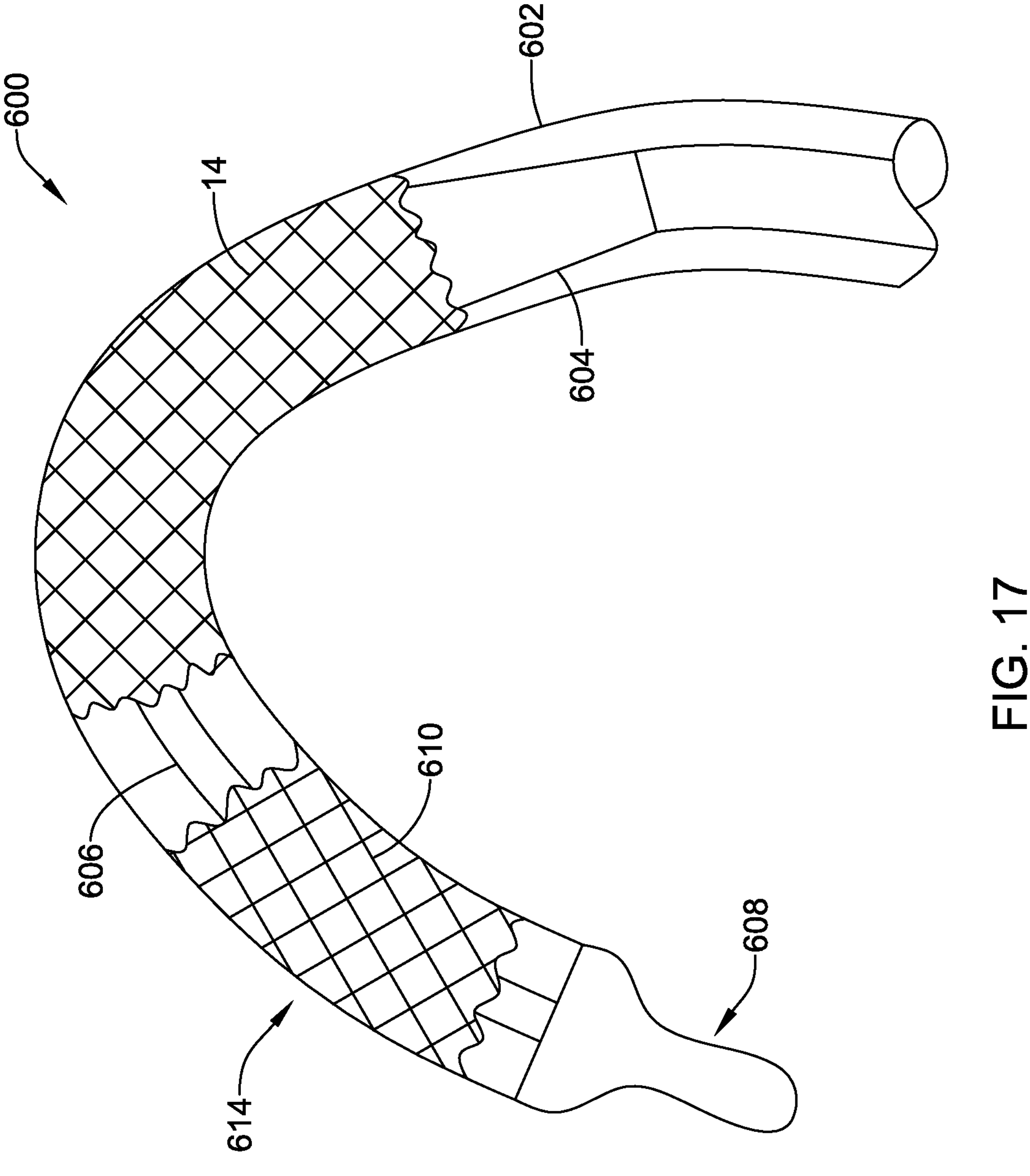
FIG. 17 is a partial cross-sectional view of an illustrative delivery system.
Figure 18:
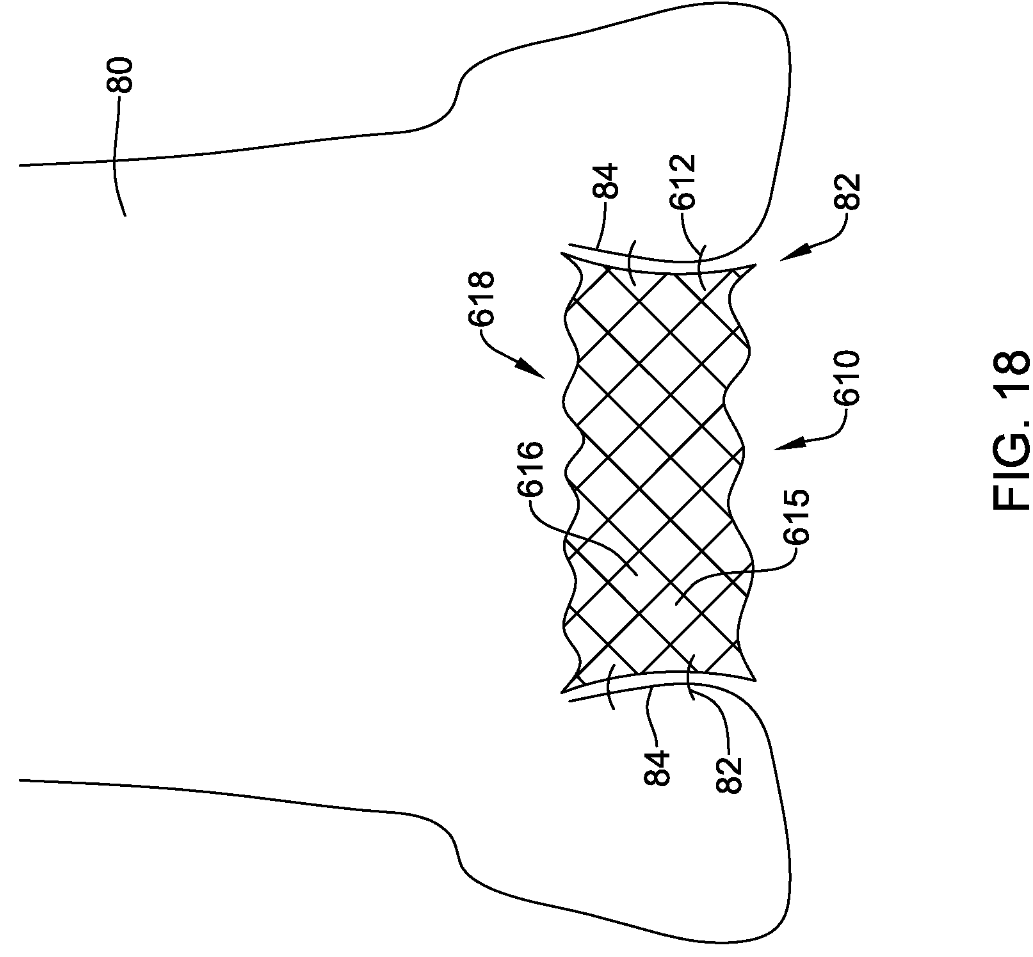
FIG. 18 is a schematic view of an illustrative docking ring in a deployed configuration within the body.
Figure 19:
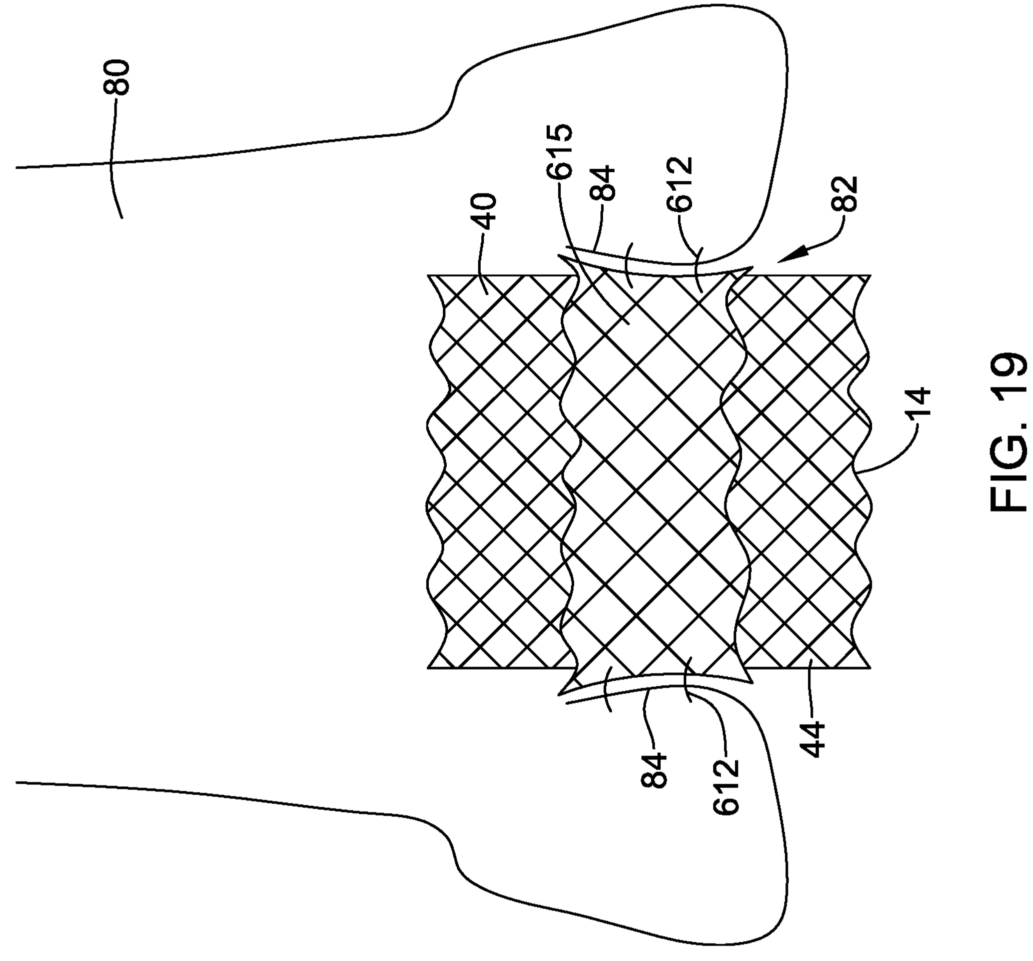
FIG. 19 is a schematic view of the illustrative implant of FIG. 1 in a deployed configuration within the body with the docking ring of FIG. 18.

FIGS. 17-19 illustrate another an alternative method and system for anchoring a medical implant 14 at or near the aortic valve 82. While FIGS. 17-19 are described with respect to the aortic valve 82, it is contemplated that the method and system may be used in other anatomical locations, as desired. Generally, the system 600 may be configured to first deliver a docking ring 610 with securement barbs 612 that engage with the native valve leaflets 84. The medical implant 14 may then be delivered within lumen of the docking member 610. Frictional engagement between the inner surface of the docking ring 610 and the outer surface of the medical implant 14 may reduce or prevent proximal and/or distal movement of the medical implant 14.

The delivery system 600 may include an outer sheath 602 configured to constrain both a medical implant 14 and a docking ring 610 in a radially collapsed delivery configuration. The medical implant 14 may be disposed over an inner tubular member 604. An inner elongate shaft 606 may be slidably disposed within the inner tubular member 604. In some cases, the docking ring 610 may be disposed over the inner tubular member 604 or the inner elongate shaft 606, as desired. A nose cone 608 may be coupled to the inner elongate shaft 606.

Generally, the delivery system 600 may be advanced to the aortic arch 80 in a similar manner to the delivery system 12 described herein. Once a distal end region 614 is positioned adjacent the aortic valve 82, the outer sheath 602 may be proximally retracted to expose the docking ring 610 (or the docking ring 610 may be distally advanced relative to the outer sheath 602). The docking ring 610 may be formed from a shape memory or superelastic material, such as, but not limited to, nitinol, so that the docking ring 610 is self-expanding upon deployment. Other suitable materials may also be used, as desired.

Referring additionally to FIG. 18, which is a schematic illustration of the docking ring 610 deployed within the aortic valve 82, the docking ring 610 may engage the native valve leaflets 84. The docking ring 610 may be a tubular member including a plurality of apertures, such as, but not limited to, laser cut tubular member or braided filament 615 having a stent-like structure. The docking ring 610 is actuatable between a "delivery" configuration (e.g., as shown in FIG. 17) and a "released" configuration. In some embodiments, the docking ring 610 may be substantially cylindrical in shape or configuration. The docking ring 610 may include one or more securement barbs 612 extending radially from an outer surface thereof. The securement barbs 612 may be curved hook like structures configured to penetrate or otherwise engage the native valve leaflets 84. In some cases, the securement barbs 612 may have a curved shape configured to resist movement in line with the flow of blood. For example, the securement barbs 612 may be shaped such that the flow of blood assists securement of the docking ring 610. The docking ring 610 may further include an outer and/or inner covering or seal 616. The seal 616 may facilitate frictional engagement between the docking ring 610 and the medical implant 14.

Once the docking ring 610 has be actuated into the released configuration, the delivery system 600 may be distally advanced through a lumen 618 of the docking ring 610 such that the medical implant 14 is adjacent to the docking ring 610. The delivery system 600 may be withdrawn or retracted to expose the medical implant 14 (or the medical implant 14 may be advanced distally relative to the delivery system 600). Then, the medical implant 14 is axially shortened and/or radially expanded from the delivery configuration to an expanded or deployed configuration, as shown in FIG. 19. Once the medical implant 14 is fully locked, the medical implant 14 may be a fully functional valve capable of maintaining hemodynamic stability while still being coupled to the delivery system 600.

Once expanded, the outer surface of the medical implant 14 may contact and frictionally engage an inner surface of the docking ring 610. For example, the seal 44 of the medical implant 14 may engage the seal 616 of the docking ring 610. The frictional engagement between the medical implant 14 and the anchored docking ring 610 anchors the medical implant in the desired location. In some cases, the seal 44 of the medical implant and/or the seal 616 of the docking ring 610 may include features to increase the friction therebetween. For example, seals 44, 616 may be treated with a coating to make the surfaces thereof tacky and resistant to relative movement. In other examples, one or more of the seals 44, 616 may include surface roughening treatments to impart features such as, but not limited to, grooves, dimples, ridges, etc. to increase the surface area thereof and thus friction engagement.

Once the docking ring 610 and the medical implant 14 have been deployed, the clinician may test the stability of the medical implant 14. If the medical implant 14 is not stable or considered to be at risk of dislodgment, the clinician recapture and reposition the medical implant to a more desirable location. Once the medical implant 14 is stable, the clinician may then move the medical implant 14 from the "deployed" configuration to the "released" configuration, as shown in FIG. 19. After the medical implant 14 is released, the delivery system 600 and any other components (including but not limited to the pigtail catheters, guidewires, etc.) may be removed, if they have not already been removed.

In some embodiments, the delivery systems 12, 600 and/or the medical implant 14, fixation mechanisms 104, 270, 400, 450, 500, and/or docking ring 610 and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "super-elastic plateau"

or "flag region" in its stress/strain curve like super-elastic nitinol does. Instead, in the linear elastic and/or non- super-elastic nitinol, as recoverable strain increases, the stress continues to increase in a substantially linear, or a somewhat, but not necessarily entirely linear relationship until plastic deformation begins or at least in a relationship that is more linear than the super-elastic plateau and/or flag region that may be seen with super-elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non- super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel- titanium alloy is FHP-NT alloy commercially available from Furukawa Techno Material Co. of Kanagawa, Japan. Other suitable materials may include ULTANIUM® (available from Neo-Metrics) and GUM METAL® (available from Toyota). In some other embodiments, a super-elastic alloy, for example a super-elastic nitinol can be used to achieve desired properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery systems 12, 600 and/or the medical implant 14, fixation mechanisms 104, 270, 400, 450, 500, and/or docking ring 610 and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical implant system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical implant system 10 to achieve the same result.

In some embodiments, a degree of Magnetic Resonance Imaging (Mill) compatibility is imparted into the medical implant system 10. For example, the delivery systems 12, 600 and/or the medical implant 14, fixation mechanisms 104, 270, 400, 450, 500, and/or docking ring 610 and/or components or portions thereof, may be made of a material that does not substantially distort the image and create substantial artifacts (i.e., gaps in the image). Certain ferromagnetic materials, for example, may not be suitable because they may create artifacts in an MRI image. The delivery systems 12, 600 and/or the medical implant 14, fixation mechanisms 104, 270, 400, 450, 500, and/or docking ring 610 and/or components or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the delivery system 12 that may define a generally smooth outer surface for the medical implant system 10. In other embodiments, however, such a sheath or covering may be absent from a portion of all of the medical implant system 10, such that the delivery system 12 may form an outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, an exterior surface of the medical implant system 10 (including, for example, the exterior surface of the delivery system 12) may be sandblasted, bead blasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of the delivery system 12, or other portions of the medical implant system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A method for securing a valve replacement implant at a valve, the method comprising:

advancing a delivery system through a vasculature to a target location;

proximally retracting the delivery system to expose a valve replacement implant carried within a lumen of the delivery system, the valve replacement implant including a plurality of valve leaflets secured to an expandable tubular anchor member;

radially expanding the valve replacement implant from a collapsed delivery configuration to an expanded deployed configuration adjacent an inner surface of a plurality of native valve leaflets;

after radially expanding the valve replacement implant into direct contact with the inner surface of all of the plurality of native valve leaflets, then advancing a pigtail catheter through the vasculature to a position adjacent an outer surface of a first one of the plurality of native valve leaflets, without advancing the pigtail catheter through the expanded valve replacement implant;

deploying a first fixation member from the pigtail catheter such that a first portion of the first fixation member engages the first native valve leaflet and a second portion of the first fixation member engages the valve replacement implant, wherein the first fixation member passes first completely through the first native valve leaflet and then through the valve replacement implant; and after deploying the first fixation member, then releasing the valve replacement implant from the delivery system.

2. The method of claim 1, wherein at least a portion of the first fixation member is radially expandable from a delivery configuration to a deployed configuration.

3. The method of claim 1, wherein the first portion of the first fixation member is configured to be positioned adjacent to an inner surface of the valve replacement implant and the second portion of the first fixation member is configured to be positioned outside the valve replacement implant.

4. The method of claim 1, wherein the first fixation member comprises a first expandable basket, a second expandable basket, and an elongate connecting member extending therebetween.

5. The method of claim 1, wherein the first fixation member comprises a helical winding.

6. The method of claim 1, wherein the first fixation member comprises a first retaining feature, a second retaining feature, and an elastic coil extending between the first and second retaining features.

7. The method of claim 1, wherein the first fixation member comprises one or more curved tines interconnected through a ring.

8. The method of claim 1, wherein the pigtail catheter comprises a delivery needle.

9. The method of claim 1, further comprising deploying a second fixation member and a third fixation member.

10. The method of claim 9, wherein the second fixation member is configured to engage a second native valve leaflet, and the third fixation member is configured to engage a third native valve leaflet.

11. The method of claim 1, wherein the pigtail catheter comprises a side port disposed proximal of a distal tip of the pigtail catheter.

12. The method of claim 11, wherein deploying a first fixation member from the pigtail catheter comprises deploying the first fixation member from the side port.

13. The method of claim 1, wherein a distal end region of the pigtail catheter is configured to assume a curved pigtail shape when unconstrained.

14. The method of claim 13, further comprising positioning the distal end region of the pigtail catheter against a cusp of the valve.

15. The method of claim 1, wherein radially expanding the valve replacement implant includes expanding it such that no part of the valve replacement implant contacts an outer surface of any native valve leaflet.

* * * * *